(12) United States Patent
Blais et al.

(10) Patent No.: US 8,614,097 B2
(45) Date of Patent: *Dec. 24, 2013

(54) METHOD AND ASSEMBLY FOR DETERMINING THE TEMPERATURE OF A TEST SENSOR

(71) Applicant: Bayer Healthcare LLC, Tarrytown, NY (US)

(72) Inventors: Jeffrey D. Blais, Walden, NY (US); Steve Sun, Mount Kisco, NY (US); Bern Harrison, Granger, IN (US); Narasinha C. Parasnis, Danbury, CT (US); Serban F. Peteu, East Lansing, MI (US); Tony Nguyen, Valhalla, NY (US); Paul Ripley, Nanuet, NY (US); Xin Wang, Elmsford, NY (US); Igor Gofman, Croton-on-Hudson, NY (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/669,034

(22) Filed: Nov. 5, 2012

(65) Prior Publication Data

US 2013/0061663 A1    Mar. 14, 2013

Related U.S. Application Data

(63) Continuation of application No. 13/339,533, filed on Dec. 29, 2011, now Pat. No. 8,313,951, which is a continuation of application No. 12/252,348, filed on Oct. 15, 2008, now Pat. No. 8,105,841.

(60) Provisional application No. 60/980,086, filed on Oct. 15, 2007, provisional application No. 61/050,101, filed on May 2, 2008.

(51) Int. Cl.
*G01N 25/20* (2006.01)
*G01N 25/48* (2006.01)

(52) U.S. Cl.
USPC .......... 436/147; 436/63; 422/82.12; 374/120; 374/121; 374/141; 374/142; 73/61.76

(58) Field of Classification Search
USPC ................... 436/63, 95, 147, 164; 422/82.12; 435/14; 374/120, 121, 131, 141, 142; 600/474, 549
See application file for complete search history.

(56) References Cited

U.S. PATENT DOCUMENTS 4,560,286 A   12/1985   Wickersheim ................. 374/131
4,575,259 A    3/1986   Bacci et al. .................... 374/130

(Continued)

FOREIGN PATENT DOCUMENTS

JP    4-175655      6/1992
JP    2007-139660   6/2007
WO    2006/109453   10/2006    ............. A61B 5/151

OTHER PUBLICATIONS

International Search Report mailed Jan. 2, 2009 issued in corresponding International Patent Application No. PCT/US2008/080055 (2 pages).

(Continued)

*Primary Examiner* — Maureen Wallenhorst
(74) *Attorney, Agent, or Firm* — Nixon Peabody LLP

(57) ABSTRACT

An assembly determines an analyte concentration in a sample of body fluid. The assembly includes a test sensor having a fluid-receiving area for receiving a sample of body fluid, where the fluid-receiving area contains a reagent that produces a measurable reaction with an analyte in the sample. The assembly also includes a meter having a port or opening configured to receive the test sensor; a measurement system configured to determine a measurement of the reaction between the reagent and the analyte; and a temperature-measuring system configured to determine a measurement of the test-sensor temperature when the test sensor is received into the opening. The meter determines a concentration of the analyte in the sample according to the measurement of the reaction and the measurement of the test-sensor temperature.

11 Claims, 17 Drawing Sheets

(56) References Cited

U.S. PATENT DOCUMENTS

| | | | |
|---|---|---|---|
| 4,935,345 A | 6/1990 | Guilbeau et al. | 435/14 |
| 5,972,715 A | 10/1999 | Celentano et al. | 436/164 |
| 6,063,233 A | 5/2000 | Collins et al. | 156/345.37 |
| 6,391,645 B1 | 5/2002 | Huang et al. | 436/95 |
| 6,880,968 B1 | 4/2005 | Haar | 374/131 |
| 8,105,841 B2 | 1/2012 | Blais et al. | 436/147 |
| 8,313,951 B2 | 11/2012 | Blais et al. | 436/147 |
| 2004/0059235 A1 | 3/2004 | Saadat | 600/500 |
| 2004/0152956 A1 | 8/2004 | Korman | 600/300 |
| 2006/0229502 A1 | 10/2006 | Pollock et al. | 600/300 |
| 2008/0300920 A1 | 12/2008 | Brown et al. | 705/2 |
| 2008/0301158 A1 | 12/2008 | Brown et al. | 707/100 |
| 2009/0146826 A1 | 6/2009 | Gofman et al. | 340/636.2 |
| 2010/0159610 A1 | 6/2010 | Sun et al. | 436/147 |
| 2010/0309947 A1 | 12/2010 | Parasnis et al. | 374/1 |
| 2010/0319436 A1 | 12/2010 | Sun et al. | 73/61.46 |
| 2011/0191059 A1 | 8/2011 | Farrell et al. | 702/130 |

OTHER PUBLICATIONS

International Written Opinion mailed Jan. 2, 2009 issued in corresponding International Patent Application No. PCT/US2008/080055 (5 pages).

Extended European Search Report mailed Mar. 18, 2011 issued in corresponding European Patent Application No. 08840230.0 (9 pages).

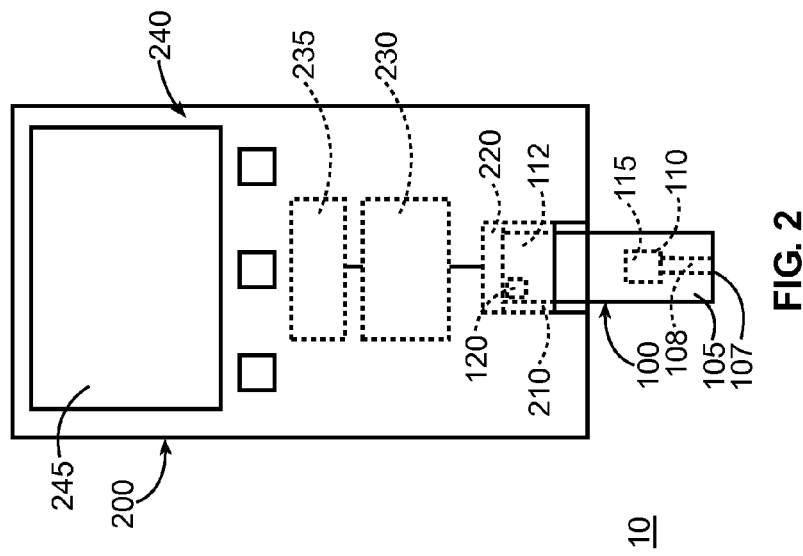
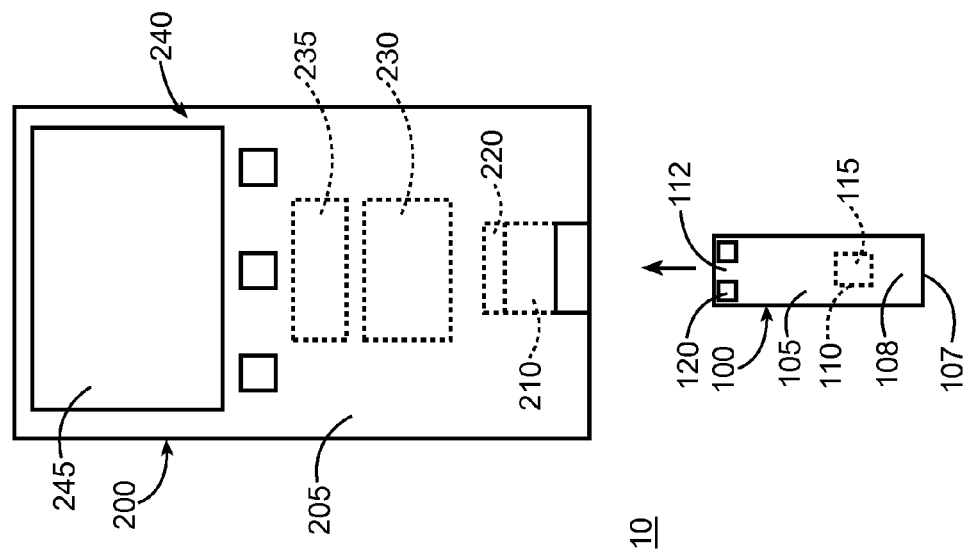

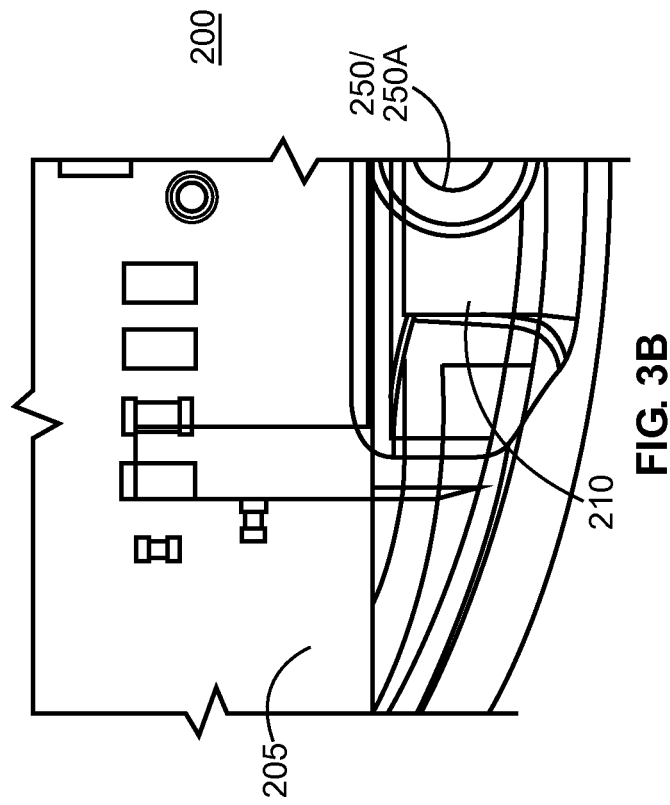
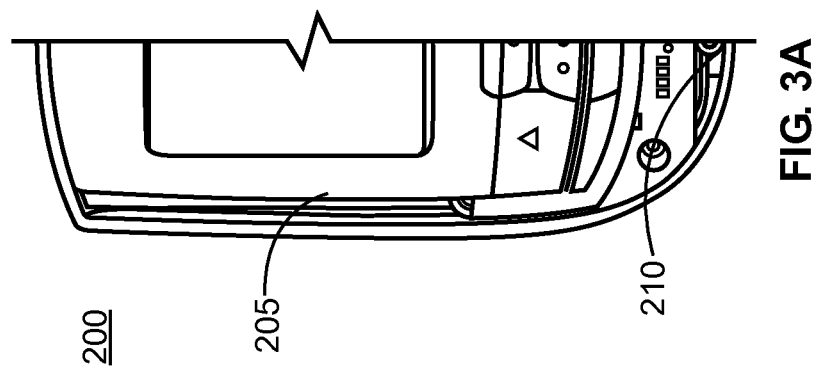

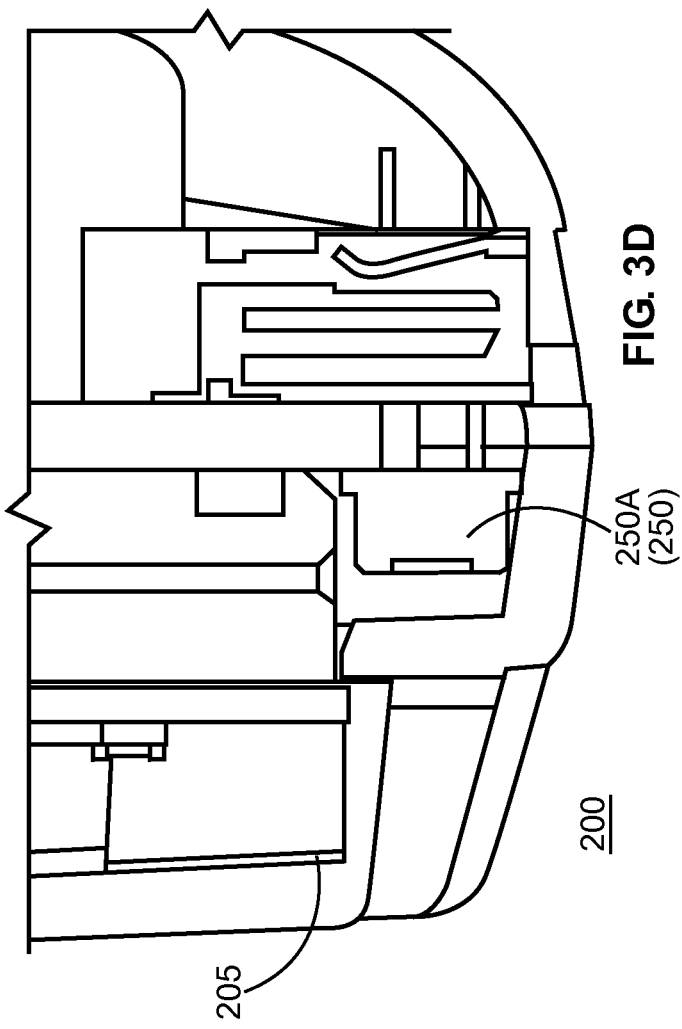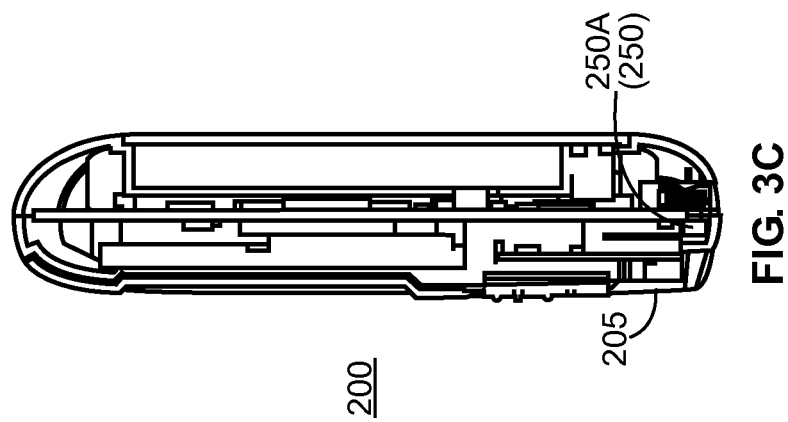

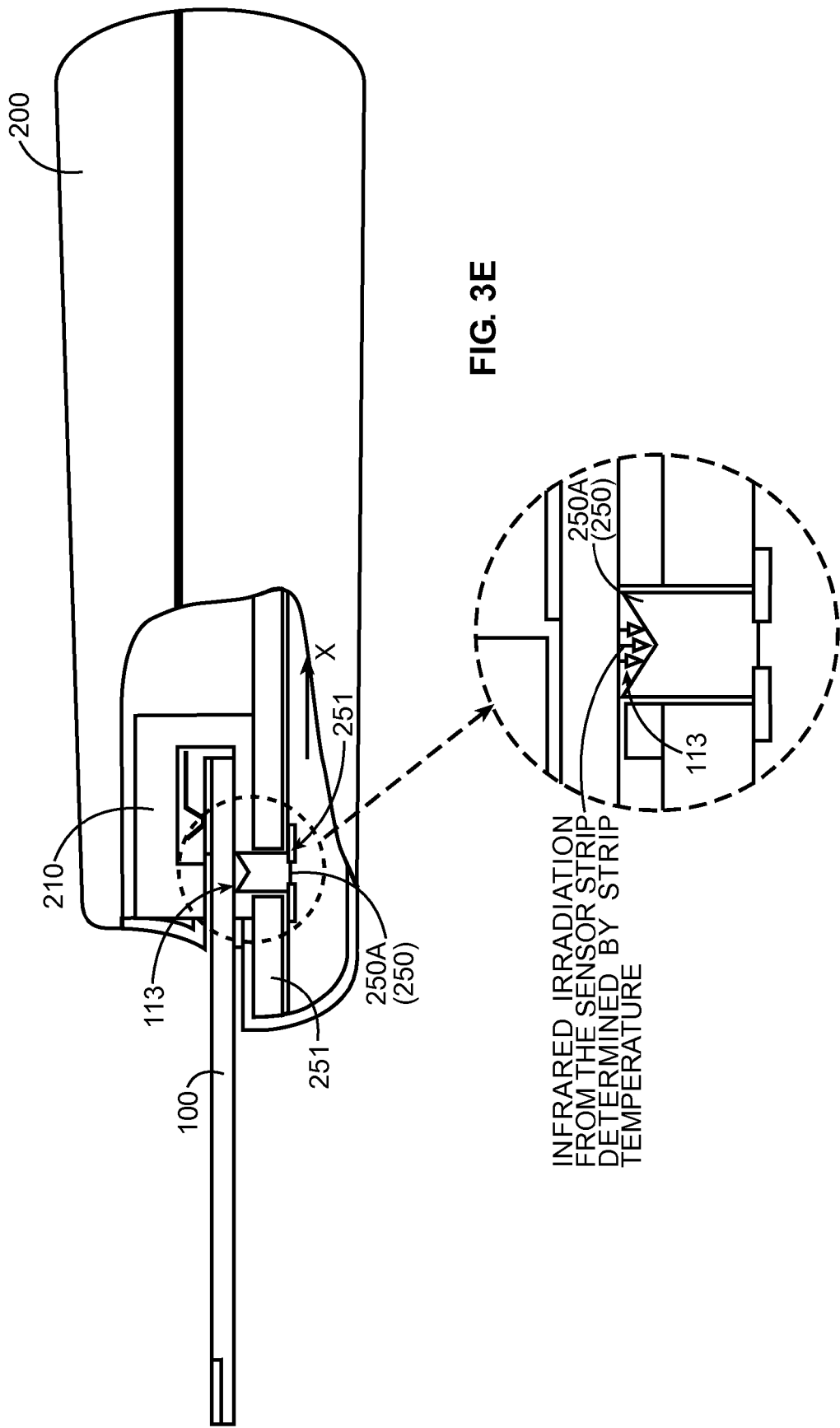

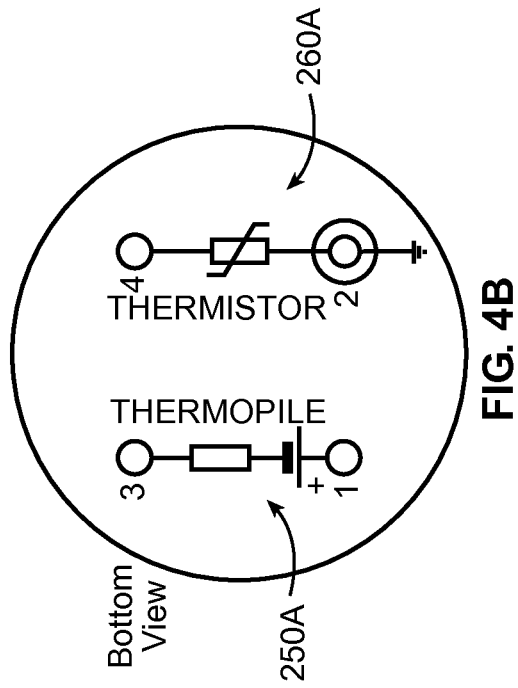
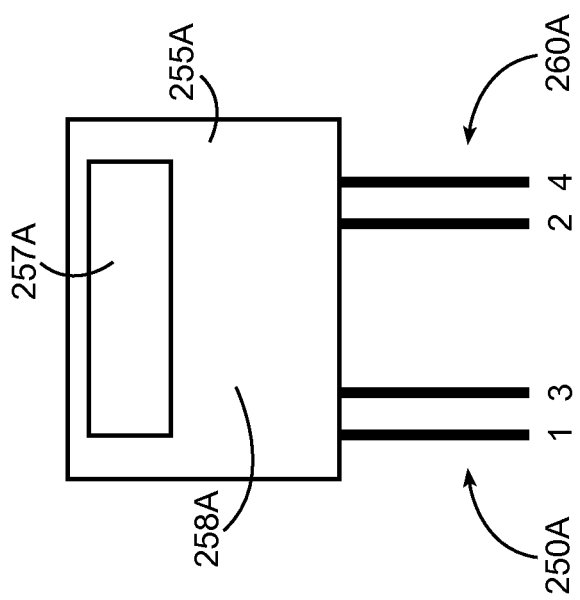
FIG. 4B
FIG. 4A

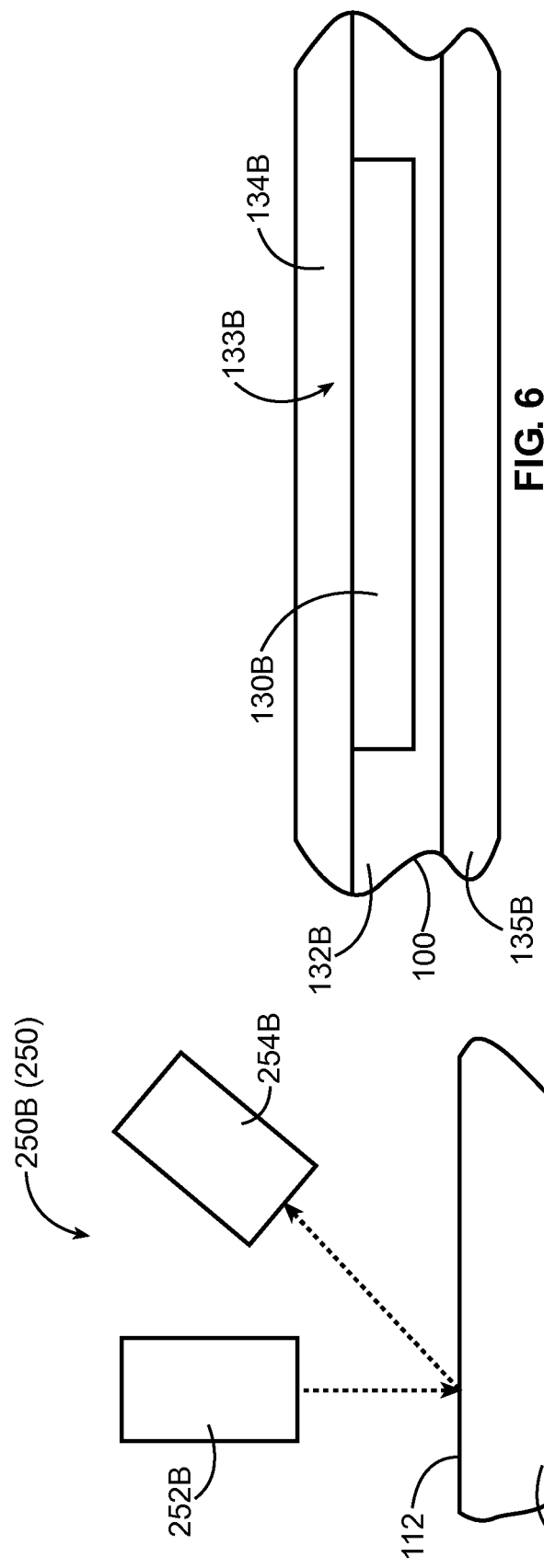

Temperature vs. time and optical intensity (RGB) data vs. time for 5-20°C.

Temperature vs. time and optical intensity (RGB) data vs. time for 20-40°C.

Temperature vs. color intensity (RGB) data for 20–40°C.

TCLC-based temperature and thermocouple data for 20-40°C.

METHOD AND ASSEMBLY FOR DETERMINING THE TEMPERATURE OF A TEST SENSOR

CROSS REFERENCE TO RELATED APPLICATIONS

This application is a Continuation Application of U.S. patent application Ser. No. 13/339,533, filed Dec. 29, 2011, now U.S. Pat. No. 8,313,951, issued on Nov. 20, 2012, which is a continuation of U.S. patent application Ser. No. 12/252,348, filed Oct. 15, 2008 and issued as U.S. Pat. No. 8,105,841 on Jan. 31, 2012, which claims the benefit of U.S. Provisional Application No. 60/980,086, filed Oct. 15, 2007, and U.S. Provisional Application No. 61/050,101, filed May 2, 2008, the contents of these applications being incorporated herein by reference.

FIELD OF THE INVENTION

The present invention generally relates to a method and assembly for determining an analyte concentration in a sample of body fluid collected on a test sensor. More specifically, the present invention generally relates to a method and assembly for measuring the temperature of the test sensor to determine the temperature of a reagent reacting with the analyte and to achieve an accurate determination of the analyte concentration based on the reaction with the reagent.

BACKGROUND OF THE INVENTION

The quantitative determination of analytes in body fluids is of great importance in the diagnoses and maintenance of certain physiological abnormalities. For example, lactate, cholesterol and bilirubin are monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with, for example, blood glucose. For example, the testing end of the sensor may be adapted to be placed into contact with the fluid being tested (e.g., blood) that has accumulated on a person's finger after the finger has been pricked. The fluid may be drawn into a capillary channel that extends in the sensor from the testing end to the reagent material by capillary action so that a sufficient amount of fluid to be tested is drawn into the sensor. The tests are typically performed using a meter that receives the test sensor into a test-sensor opening and applies optical or electrochemical testing methods.

The accuracy of such testing methods however may be affected by the temperature of the test sensor. For example, the result of the chemical reaction between blood glucose and a reagent on a test sensor may vary at different temperatures. To achieve an accurate reading, the actual measurement is corrected based on the actual sensor temperature, taken right before the reaction begins. The conventional way to measure the test sensor temperature involves reading a resistive value from a thermistor placed near the test-sensor opening. The thermistor resistance recalculates the chemical reaction result. This correction method is based on an assumption that a sensor temperature is the same as the thermistor temperature placed near the test-sensor opening. In reality, however, the thermistor, which is typically located on a printed circuit board, actually provides the temperature of the meter. Because the temperature of the meter can be very different from the test sensor temperature, the analyte measurement may be inaccurate.

As a result, it would be desirable to have a method and assembly that accurately measures and accounts for the temperature of the test sensor for achieving an accurate analyte measurement.

SUMMARY OF THE INVENTION

Reagents that are used to measure analyte concentration in a sample of body fluid may be sensitive to changes in temperature. In other words, the magnitude of the reaction between the reagent and the analyte may depend on the temperature of the reagent. As a result, any calculation of the analyte concentration in the sample based on the reaction may vary with the temperature of the reagent. Accordingly, to achieve a more accurate measurement of the analyte concentration, some embodiments of the present invention also determine the temperature of the reagent. The temperature of the reagent is used by an algorithm which determines the analyte concentration. Embodiments may determine the reagent temperature by measuring the temperature of a test sensor that holds the reagent in a fluid-receiving area for reaction with a collected sample. In particular, these embodiments measure the test-sensor temperature while the area of the test sensor being measured is in equilibrium with the reagent temperature.

One embodiment provides an assembly for determining an analyte concentration in a sample of body fluid. The assembly includes a test sensor having a fluid-receiving area for receiving a sample of body fluid, where the fluid-receiving area contains a reagent that produces a measurable reaction with an analyte in the sample. The assembly also includes a meter having a port or opening configured to receive the test sensor; a measurement system configured to determine a measurement of the reaction between the reagent and the analyte; and a temperature-measuring system configured to determine a measurement of the test-sensor temperature when the test sensor is received into the opening. The meter determines a concentration of the analyte in the sample according to the measurement of the reaction and the measurement of the test-sensor temperature.

Another embodiment provides a method for determining an analyte concentration in a sample of body fluid. The method includes receiving a test sensor into a port or opening. The test sensor has a fluid-receiving area for receiving a sample of body fluid, and the fluid-receiving area contains a reagent that produces a measurable reaction with an analyte in the sample. The method also includes determining a measurement of the test-sensor temperature when the test sensor is received into the opening. Furthermore, the method includes determining a concentration of the analyte in the sample according to the measurement of the reaction and the measurement of the test-sensor temperature.

BRIEF DESCRIPTION OF THE DRAWINGS

FIG. 1 illustrates a general diagnostic system, including a test sensor and a meter, according to an embodiment of the present invention.

FIG. 2 illustrates the embodiment of FIG. 1 with the test sensor inserted into the meter.

FIG. 3A illustrates a partial plan view of a meter according to an embodiment of the present invention.

FIG. 3B illustrates an enlarged transparent partial view of the meter of FIG. 3A.

FIG. 3C illustrates an internal side view of the meter of FIG. 3A.

FIG. 3D illustrates yet another internal view of the meter of FIG. 3A.

FIG. 3E illustrates yet another internal view of the meter of FIG. 3A.

FIG. 4A illustrates a thermopile sensor and a thermistor that may be used by an embodiment of the present invention.

FIG. 4B illustrates a bottom view of the thermopile sensor and the thermistor of FIG. 4A.

FIG. 5 illustrates a configuration for an optical-sensing system that may be used by an embodiment of the present invention.

FIG. 6 illustrates a view of a test sensor employing a thermochromic liquid crystals according to an embodiment of the present invention.

Figure 3F:
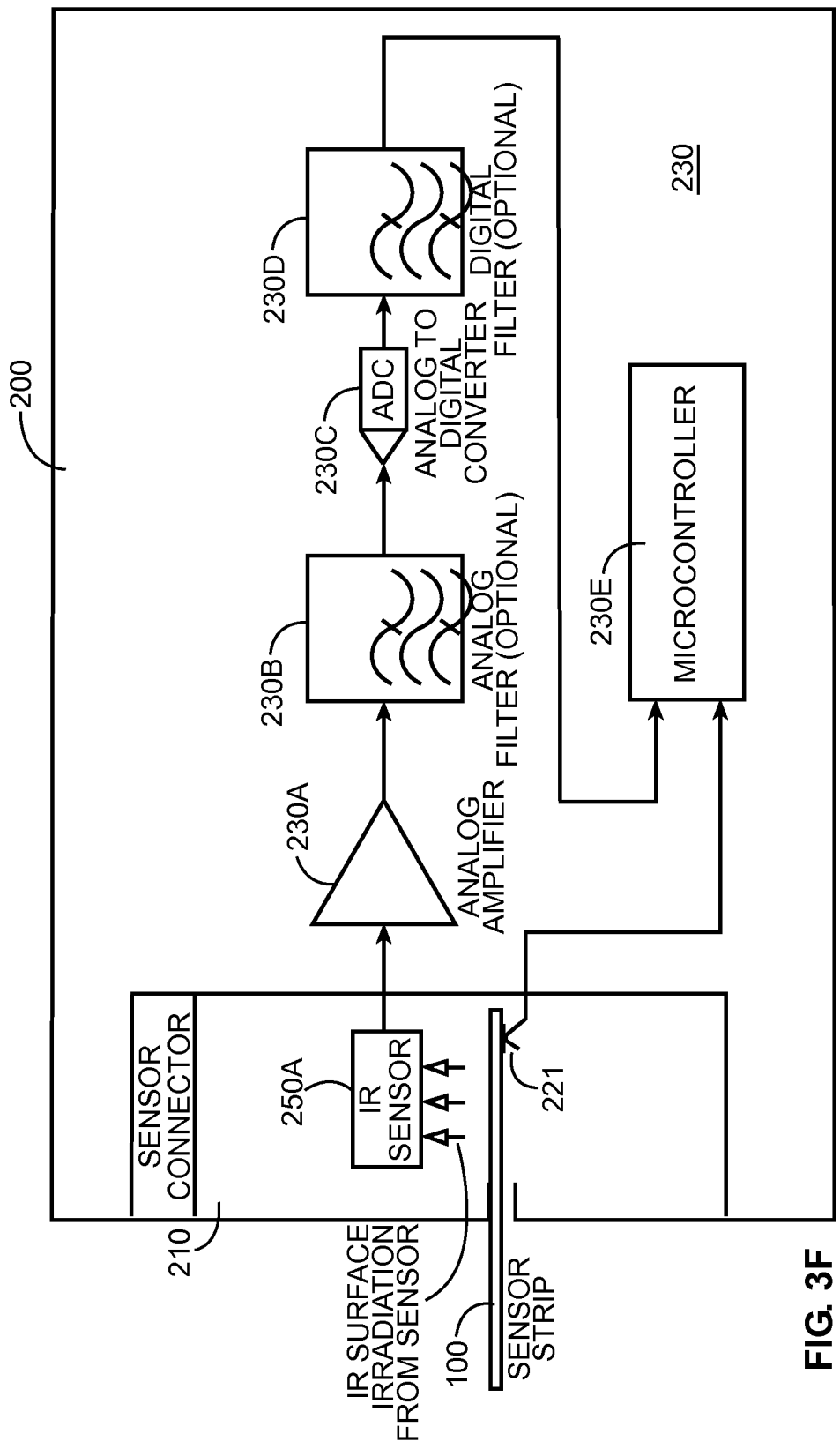
FIG. 3F illustrates an example processing system for the meter of FIG. 3A.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF ILLUSTRATED EMBODIMENTS

Aspects of the present invention provide methods and assemblies for measuring the temperature of a reagent on a test sensor used to collect a sample of body fluid. The reagent reacts with an analyte in the sample of body fluid and the level of reaction may be measured to determine the concentration of analyte in the sample. The level of reaction may be affected by changes in temperature of the reagent. By measuring the temperature of the reagent, aspects of the present invention may account for the reagent's sensitivity to temperature and thus obtain a more accurate calculation of the concentration of analyte in the sample.

Referring to FIG. 1, a diagnostic system 10 with a test sensor 100 and a meter 200 is illustrated. The test sensor 100 is configured to receive a fluid sample and is analyzed using the meter 200. Analytes that may be analyzed include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

As shown in FIG. 1, the test sensor 100 includes a body 105 having a fluid-receiving area 110 for receiving a sample of body fluid. For example, a user may employ a lancet or a lancing device to pierce a finger or other area of the body to produce the blood sample at the skin surface. The user may then collect this blood sample by placing an opening 107 of the test sensor 100 into contact with the sample. The blood sample may flow from the opening 107 to the fluid-receiving area 110 via a capillary channel 108, as generally depicted in the embodiment of FIG. 1. The fluid-receiving area 110 may contain a reagent 115 which reacts with the sample to indicate the concentration of an analyte in the sample. The test sensor 100 also has a meter-contact area 112 which is received by the meter 200 as described in detail further below.

The test sensor 100 may be an electrochemical test sensor. An electrochemical test sensor typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. In general, the enzyme is selected to react with the desired analyte or analytes to be tested so as to assist in determining an analyte concentration of a fluid sample. If the concentration of another analyte is to be determined, an appropriate enzyme is selected to react with the analyte. Examples of electrochemical test sensors, including their operation, may be found in, for example, U.S. Pat. No. 6,531,040 assigned to Bayer Corporation. It is contemplated, however, that other electrochemical test sensors may be employed.

Alternatively, the test sensor 100 may be an optical test sensor. Optical test sensor systems may use techniques such as, for example, transmission spectroscopy, diffuse reflectance, or fluorescence spectroscopy for measuring the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid. The color change of the sample is evaluated to measure the absorbance level of the transmitted light. Transmission spectroscopy is described in, for example, U.S. Pat. No. 5,866,349. Diffuse reflectance and fluorescence spectroscopy are described in, for example, U.S. Pat. Nos. 5,518,689 (titled "Diffuse Light Reflectance Read Head"), 5,611,999 (titled "Diffuse Light Reflectance Read Head"), and 5,194,393 (titled "Optical Biosensor and Method of Use").

As further illustrated in FIG. 1, the meter 200 includes a body portion 205 with a test sensor opening 210, which includes a connector for receiving and/or holding a test sensor 100. The meter 200 also includes a measurement system 220 for measuring the concentration of analyte for the sample in fluid-receiving area 110. For example, the measurement system 220 may include contacts for the electrodes to detect the electrochemical reaction for an electrochemical test sensor. Alternatively, the measurement system 220 may include an optical detector to detect the chromatic reaction for an optical test sensor. To process information from the measurement system 220 and to generally control the operation of the meter 200, the meter 200 may employ at least one processing system 230, which may execute programmed instructions according to a measurement algorithm. Data processed by the processing system 230 may be stored in a conventional memory device 235. Furthermore, the meter may have a user interface 240 which includes a display 245, which, for example, may be a liquid-crystal display. Pushbuttons, a scroll wheel, touch screens, or any combination thereof, may also be provided as a part of the user interface 240 to allow a user to interact with the meter 200. The display 245 typically shows information regarding the testing procedure and/or information in response to signals input by the user. The result of the testing may also be announced audibly, by, for example, using a speaker.

In general operation, a user removes a test sensor 100 from a package, such as a container, at time $t_0$. The user then inserts the test sensor 100 into the test-sensor opening 210 at time $t_1$, as shown in FIG. 2. Upon insertion of the test sensor 100 at time $t_1$, the meter 200 is activated, i.e. wakes up, to begin a predefined testing procedure according to one method. In particular, a signal is sent from the test-sensor opening 210 to wake up the measurement system 220. This signal, for example, may be mechanically or electrically generated. The user then places the test sensor 100 at time $t_s$ into contact with a sample of body fluid, which is received into the fluid-receiving area 110. The sample then reacts with the reagent 115, and the measurement system 220 measures the level of reaction. The processing system 230 receives information on the reaction, e.g. in the form of a electrical signal, and determines the amount of analyte concentration in the sample according to the measurement algorithm. The results of this measurement may then be recorded in memory device 235 and/or displayed to the user via the display 245.

Diagnostic systems, such as blood-glucose testing systems, typically calculate the actual glucose value based on a measured output and the known reactivity of the reagent-sensing element (e.g., test sensor 100) used to perform the test. Calibration information is generally used to compensate for different characteristics of test sensors, which will vary on a batch-to-batch basis. The calibration information may be, for example, the lot specific reagent calibration information for the test sensor. The calibration information may be in the form of a calibration code. Selected information associated with the test sensor (which may vary on a batch-to-batch basis) is tested to determine the calibration information to be used in association with the meter. The reactivity or lot-calibration information of the test sensor may be provided on a calibration circuit that is associated with the sensor package or the test sensor. This calibration circuit may be inserted by the end user. In other cases, the calibration is automatically done using an auto-calibration circuit via a label on the sensor package or the test sensor. In these cases, calibration is transparent to the end user and does not require that the end user insert a calibration circuit into the meter or enter coding information. Some embodiments of the present invention may provide either a manual- or auto-calibrating diagnostic system. In the example shown in FIG. 1, the diagnostic system 10 is auto-calibrating, so the test sensor 100 may include an auto-calibration information area 120, which may include a label, at the meter-contact area 112.

As discussed previously, the temperature of the reagent on the test sensor 100 may affect the accuracy of the concentration of analyte calculated by the meter 200, as the level of reaction between the analyte and the reagent 115 may be dependent on the temperature of the reagent 115. As such, some embodiments of the present invention determine a temperature for the reagent 115 and use this calculated temperature to produce a more accurate measurement of the analyte concentration. In particular, the meter 200 has a temperature-measuring system 250 and the processing system 230 uses this calculated temperature from the temperature-measuring system 250 as a variable input for a measurement algorithm.

In operation, when a test sensor 100 is inserted at time $t_1$ into the test-sensor opening 210 of the meter, the temperature of the test sensor 100 is also measured with the temperature-measuring system 250. Although the system 250 may actually measure the temperature of the test sensor 100, i.e., the meter-contact area 112, instead of the temperature of the reagent 115, the temperatures of the test sensor 100 and the reagent 115 are generally at equilibrium with the ambient temperature when the test sensor 100 is inserted into the test-sensor opening 210 at time $t_1$. As shown in FIG. 2, when the test sensor 100 is inserted into the test-sensor opening 210, the meter-contact area 112 is positioned in the test-sensor opening 210, but the fluid-receiving area 110 may be positioned distally from the meter 200. As such, the meter-contact area 112 may be heated by sources of heat in the meter 200, such as components receiving power from a power source. However, the fluid-receiving area 110 and the reagent 115 may be sufficiently spaced from the sources of heat to remain substantially at ambient temperature. Thus, determining the ambient temperature provides a useful estimate of the temperature of the reagent 115, which is used as a factor in determining analyte concentration. It is noted that for a brief time, the temperature of the fluid-receiving area 110 may increase at time $t_s$ when it receives the fluid sample, which may retain some heat from the body. It has been determined that for a short time period, e.g., approximately 0.5 seconds to approximately 5 seconds, after the test sensor 100 has been inserted into the test-sensor opening 210 at time $t_1$, the ambient temperature can still be determined from the meter-contact area 112 before the temperature of the area 112 increases due to heat from the meter 200 or decreases due to cooling from the meter 200. The time period for determining the ambient temperature from the meter-contact area 112 may vary from the time that the test sensor is inserted, e.g., approximately 0.5 seconds to approximately 5 seconds, depending on factors, such as the type of meter being used, etc. It is understood that the time range provided here, i.e., approximately 0.5 seconds to approximately 5 seconds, is provided as an example and that other time periods may be appropriate. Other such factors are discussed further below. Accordingly, some embodiments of the present invention may measure the temperature of area 112 at time $t_1$ when the effects of heat or cooling from the meter 200 are still at a minimum.

Although some embodiments may measure the temperature of area 112 at time t₁ described above, other embodiments may measure the temperature at other times. Even if the effects of heat or cooling from the meter 200 have already changed the temperature of the area 112 at the time of measurement, the temperature of the area 112 prior to the effects of heat or cooling may be determined by applying an algorithm to the measurement. For example, the temperature as a function of time, i.e., a temperature-time curve, may be applied to extrapolate backwards from the measurement to determine a temperature at time $t_1$, before the actual measurement time.

As shown in FIG. 2 and FIGS. 3A-E, the temperature-measuring system 250 is positioned in the test-sensor opening 210 of the meter body 205, such that the temperature-measuring system 250 may be positioned in proximity to the test sensor 100 when it is inserted into the test-sensor opening 210. In the embodiment illustrated by FIGS. 3A-E, the temperature-measuring system 250 includes a thermopile sensor 250A disposed at a position 251 within the test-sensor opening 210, for example on a printed circuit board 231.

Although some embodiments may include a temperature-measuring system 250 disposed at a position 251 within the test-sensor opening 210, a temperature-measuring system 250 may be disposed at other areas to allow temperature measurement of test sensor 100. For example, the temperature-measuring system 250 may be positioned on a structure, such as an arm, that extends outwardly from the meter body 205 to measure an area of the test sensor 100 that is positioned outside the test-sensor opening 210 when the test sensor 100 is inserted into the test-sensor opening 210. The structure may extend permanently from the meter body 205 or may be operated manually or triggered automatically to extend or swing out into an appropriate position for measuring an area of the test sensor 100. Moreover, other embodiments may include more than one structure disposed anywhere relative to the meter body 205 for measuring more than one area of the test sensor 100. Temperature measurements from more than one area may provide a more accurate determination of the temperature for the reagent 115. For example, unlike the configuration of FIG. 3E, the test sensor 100 may be inserted transversely, rather then longitudinally, into a test-sensor opening 210, so that more than one area along the test sensor 100 may be accessed to obtain temperature measurements.

In general, all materials at temperatures above absolute zero continuously emit energy. Infrared radiation is part of the electromagnetic spectrum and occupies frequencies between visible light and radio waves. The infrared (IR) part of the spectrum spans wavelengths from about 0.7 micrometers to about 1000 micrometers. The wave band usually used for temperature measurement is from about 0.7 to about 20 micrometers. The thermopile sensor 250A measures the actual sensor strip temperature by using blackbody radiation emitted from the test sensor 100. By knowing the amount of infrared energy emitted by the test sensor 100 and its emissivity, the actual temperature of the test sensor 100 can be determined. In particular, the thermopile sensor 250A may generate a voltage proportional to incident infrared radiation. Because the temperature of a surface of the test sensor 250A is related to the incident infrared radiation, the temperature of the surface can be determined from the thermopile sensor 250A.

When the test sensor 100 is received into the test-sensor opening 210, the position 251 of the thermopile sensor 250A is proximate, or substantially adjacent, to the test sensor 100. The position 251 ensures that the infrared radiation detected by the thermopile sensor 250A comes substantially from the test sensor 100. In other words, the thermopile sensor 250A may be positioned to minimize the effect of light from external sources, e.g., ambient light, on the readings of the thermopile sensor 250A. While FIG. 3E, for example, show the thermopile sensor 250A below the test sensor 100, it is understood that the thermopile sensor may be positioned in other appropriate positions relative to the test sensor.

FIG. 3F illustrates aspects of a processing system 230 that may be employed for implementing the thermopile sensor 250A in the meter 200. First, an output electrical signal from the thermopile sensor 250A is received by an analog amplifier 230A. The amplified analog signal from the analog amplifier 230A is passed to an analog-to-digital converter 230C via an analog filter 230B. The analog-to-digital converter 230C digitizes the amplified analog signal, which may subsequently be filtered by a digital filter 230D. The digital signal is then transmitted to a microcontroller 230E. The microcontroller 230E calculates the temperature of the test sensor 100 based on the magnitude of the output electrical signal from the thermopile sensor 250A and the calculated temperature is employed to correct the initial blood glucose measurement from the measurement system 220. For some embodiments, it is contemplated that the analog filter 230B, the analog-to-digital converter 230C, and the digital filter 230D may be incorporated into the microcontroller 230E. In some embodiments, the analog filter 230B and the analog-to-digital converter 230C may be integrated into an application-specific integrated circuit (ASIC). In further embodiments, a memory, such as an EEPROM, may be employed to store calibration data and the like. Moreover, it is further contemplated that in some embodiments the analog filter 230B and the digital filter 230D may be optional. It is also noted that although the thermopile sensor 250A in FIG. 3F is positioned opposite from the electrical contacts 221 that receive the test sensor electrodes, other embodiments may position the thermopile sensor to be on the same side of the test sensor.

FIGS. 4A and 4B illustrate a typical thermopile sensor 250A, which includes a series of thermal elements hermetically sealed in a metal housing 255A. In particular, the thermopile sensor 250A may include an optical filter 257A and an absorbing area 258A. It is contemplated that the thermopile sensor 250A may be housed in a variety of TO housings or surface mount device housings. The time constant for the thermopile sensor 250A is of the order of 100 ms or less, which corresponds operationally with diagnostic systems 10 which have typical test times of the order of approximately 5 seconds. In general, the thermopile sensor 250A provides sufficient sensitivity, a small temperature coefficient of sensitivity, as well as high reproducibility and reliability.

As illustrated in FIGS. 4A and 4B, the temperature-measuring system 250 may optionally include an additional reference temperature sensor 260A, such as a sensor, thermistor, semiconductor temperature sensor, or the like. This reference temperature resistor, or thermistor, 260A may also be included in the housing 255A. As such, the temperature-measuring system 250 shown in FIGS. 3A-F can provide the temperature of the test sensor 100 and the reference temperature of the meter body 205 as variable inputs for the measurement algorithm run by the processing system 230. Accordingly, the temperature-measuring system 250 of FIGS. 4A and 4B has two pins, e.g. pins 1 and 3, corresponding to the thermopile sensor 250A and two pins, e.g. pins 2 and 4, corresponding to the thermistor 260A. Thus, the meter 200 measures the voltage across the pins 1 and 3, which indicates the amount of infrared radiation associated with the temperature of the test sensor 200. In addition, the meter measures the resistance across pins 2 and 4, which indicates the temperature of the meter body 205. It is contemplated that other types of contact structures, such as pads, may be employed, and embodiments are not limited to the use of the pins shown in FIGS. 4A and 4B.

For example, the meter 200 may be equipped with a Heimann HMS Z11-F5.5 Ultrasmall Thermopile Sensor (Heimann Sensor GmbH, Dresden, Germany), which provides a Complementary Metal Oxide Semiconductor (CMOS) compatible sensor chip plus a thermistor reference chip. The HMS Z11-F5.5 is 3.55 mm in diameter and 2.4 mm in height. It is contemplated that other thermopile sensors may be used, having different dimensions. Advantageously, the compact dimensions of such a thermopile sensor enable the thermopile sensor to be packaged within known meter configurations and positioned at the test-sensor opening into which the test sensor is inserted.

In one study, a meter was configured with a Heimann HMS B21 Thermopile Sensor (Heimann Sensor GmbH). The HMS B21 Thermopile Sensor operates similar to the HMS Z11-F5.5 Ultrasmall Thermopile Sensor, described previously, but has larger dimensions, i.e., 8.2 mm in diameter and 3 mm in height. The study showed that although the meter body had a temperature of approximately 30° C., the thermopile sensor was able to measure the temperature of an inserted test strip at room temperature, i.e. approximately 20° C. It is contemplated that other thermopile sensors may be used.

In some embodiments, the temperature-measuring device 250 may also be employed to measure temperature change that indicates the actual concentration of an analyte. For instance, reaction between the analyte and the reagent may generate measurable heat that indicates the concentration of the analyte in the sample.

In an alternative embodiment, the temperature-measuring system 250 may include an optical-sensing system 250B as shown in FIG. 5. Rather than measuring infrared radiation to calculate the temperature of the test sensor 100, the meter 200 may measure changes to temperature-sensitive or thermochromic materials that are applied to the test sensor 100. Thermochromic materials change color according to changes in temperature.

In general, thermochromism is the reversible change in the spectral properties of a substance that accompanies heating and cooling. Although the actual meaning of the word specifies a visible color change, thermochromism may also include some cases for which the spectral transition is either better observed outside of the visible region or not observed in the visible at all. Thermochromism may occur in solid or liquid phase.

Light can interact with materials in the form of reflection, adsorption or scattering, and temperature-dependent modifications of each of these light-material interactions can lead to thermochromism. These thermochromic materials may include leuco dyes and cholesteric liquid crystals. Other thermocromic materials also include electroactive polymers, such as polyacetylenes, polythiophenes, or polyanilines. Classes of thermochromic materials are illustrated according to the physical background in TABLE 1.

TABLE 1

| Thermochromic Material | Material feature | Interaction |
| --- | --- | --- |
| Cholesteric liquid crystals<br>Crystalline colloidal arrays embedded in a gel network<br>Inorganic salts | Periodic structure | Reflection |
| Conjugated polymers<br>Hydrogel-indicator dye systems<br>Leuco dye-developer-solvent systems | Chromophoric group | Absorption |
| Hydrogel exhibiting LCST<br>Polymer blends exhibiting LCST | Areas with different refractive indices | Scattering |

Such temperature-sensitive materials may generally be applied on any portion of the meter-contact area 112. In the embodiment of FIG. 1, a thermochromic material may be applied to the auto-calibration information area 120. Referring back to FIG. 5, a general configuration for the optical-sensing system 250B is illustrated. The optical-sensing system 250B may include a light source 252B and a detector 254B. The light source 252B transmits photons from the thermchromic material, and the detector 254B receives the photons that are reflected from the thermchromic material. For example, the light source 252B may be one or more laser LEDs, while the detector 254B may be one or more photodiodes. For materials, such as ChromaZone (a microencapsulated thermochromic pigment) which changes from color to colorless as the temperature increases, and vice versa, the temperature can be determined by measuring the level of reflection from the material.

Although the optical-sensing system 250B may actually measure the temperature of the test sensor 100, i.e. the meter-contact area 112, instead of the temperature of the reagent 115, the temperatures of the test sensor 100 and the reagent 115 are generally at equilibrium with the ambient temperature when the test sensor 100 when the test sensor 100 is inserted into the test-sensor opening 210 at time $t_1$. As described previously, when the test sensor 100 is inserted into the test-sensor opening 210, the meter-contact area 112 is positioned in the test-sensor opening 210, but the fluid-receiving area 110 may be positioned distally from the meter 200. As such, the meter-contact area 112 may be heated by sources of heat in the meter 200, such as components receiving power from a power source. However, the fluid-receiving area 110 and the reagent 115 may be sufficiently spaced from the sources of heat to remain substantially at ambient temperature. Thus, determining the ambient temperature provides a useful estimate of the temperature of the reagent 115, which is used as a factor in determining analyte concentration. It has been determined that for a short period time, e.g., approximately 0.5 seconds to approximately 5 seconds, after the test sensor 100 has been inserted into the test-sensor opening 210 at time $t_1$, the ambient temperature can still be determined from the meter-contact area 112 before the temperature of the area 112 increases due to the heat from the meter 200 or decreases due to the cooling from the meter 200. Accordingly, some embodiments of the present invention measure the temperature of area 112 at time $t_1$ when the effects of heat or cooling from the meter 200 are still at a minimum. As described previously, other embodiments may measure the temperature at other times and account for the effects of heating or cooling from the meter 200 by applying an algorithm. Furthermore, as also described previously, alternative embodiments may include more than one structure disposed anywhere relative to the meter body 205 for measuring more than one area of the test sensor 100 inside or the outside test-sensor opening 210.

To further explain aspects of embodiments employing a thermochromic material, thermochromic liquid crystals (TCLCs) are described in detail. Thin film TCLCs are commercially available. For example, FIG. 6 illustrates a test sensor 100 that is configured to use a TCLC 130B. The TCLC 130B is applied in an area 133B that is defined by a thin cured material 132B, such as an epoxy resin, which is applied to a back layer or window 135B. A front window or substrate 134B is formed over the TCLC 130B.

Figure 12:
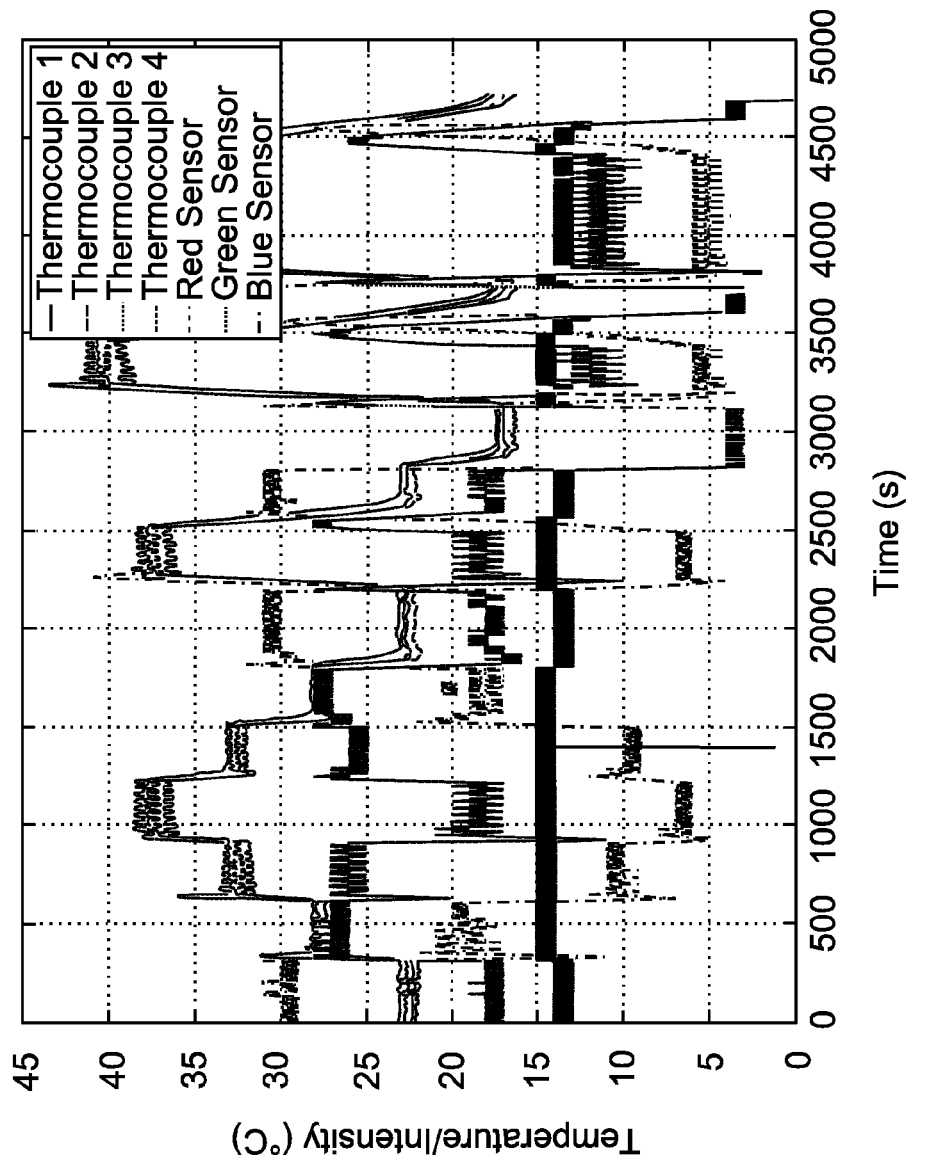
FIG. 12 illustrates a graph of temperature vs. time and optical intensity (RGB) vs. time for 20° C. to 40° C. temperature tests.

In some embodiments, an array of thermochromic materials corresponding to varying temperature ranges may be employed to measure the temperatures. For example, FIG. 12 illustrates "a sliced-pie TCLC configuration" 300 including eight TCLC circular segments 310, each being sensitive for a smaller temperature range. Eight miniature LEDs 320 are sequentially employed, and a single miniaturized RGB 330 is placed in the center to detects the corresponding color.

TCLCs may provide certain advantages over other thermochromic materials. For example, while leuco dyes may provide a wide range of colors, TCLCs may respond more precisely and can be engineered for more accuracy than leuco dyes. It is understood, however, that the examples provided herein are provided for illustrative purposes only.

TCLCs are characterized by well analyzed reflections of the visible light within a certain bandwidth of temperature. Typically, TCLC's are specified for their color play. The resulting color play is highly sensitive to changes in temperature. A certain temperature leads to a certain reflected wavelength spectrum, with a local maximum at a certain wavelength and a narrow bandwidth. Accordingly, the optical-sensing system 250B may employ a liquid crystal temperature sensor that can be optimized to read a temperature range of approximately 5° C. to 40° C., for example. In this example, the lower end of the range of 5° C. may be referred to as the "Red Start" temperature, and the higher end of 40° C. may be referred to as the "Blue Start" temperature. The bandwidth between the Red Start and Blue Start temperatures is thus 35° C. It is contemplated that Red and Blue Starts may vary from these examples.

Figure 7:
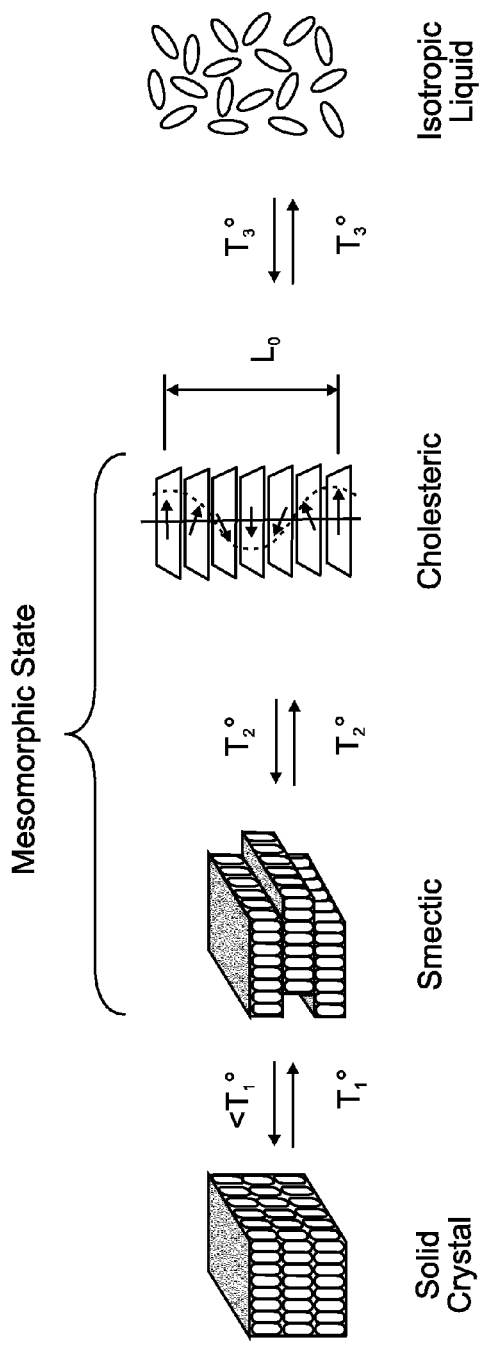
FIG. 7 illustrates molecular changes of the thermochromic liquid crystal with temperature.

When the temperature of the TCLC is below the Red Start temperature, TCLC, particularly when applied in thin layers, are optically inactive or transparent. Below the start temperature of the color change, TCLCs hydrodynamically behave like a high viscosity paste. They are transparent when applied in thin layers, or milky-white in bulk. In this initial state, the molecules are still ordered and close to each other as in a solid crystal, as shown in FIG. 7. As the temperature increases toward the Red Start temperature, the molecules are separated into layers as they pass through the Smectic phase, but in this Mesomorphic state, the crystals are still optically inactive or transparent.

Above the Red Start temperature, the molecules are in the cholesteric state, where they are optically active and reflect the light selectively and strongly depending on temperature. With increasing temperature, the light reflected from the thermochromic layer changes, in sequence, from red to orange, to yellow, to green, and then to blue. The molecules are now arranged in layers, within which the alignment is identical. In between layers, however, the molecule orientation is twisted by a certain angle. The light passing the liquid crystal (LC) undergoes Bragg defraction on these layers, and the wavelength with the greatest constructive interference is reflected back, which is perceived as a spectral color. As the crystal undergoes changes in temperature, thermal expansion occurs, resulting in change of spacing between the layers, and therefore in the reflected wavelength. Specifically, cumulatively an overall helix-shaped architecture is formed, and the molecular director traces out a helix in space. The degree of twist is defined by the pitch length $L_0$, which is the height of the helical structure after one 360° rotation. The angle between two layers and thereby the pitch length of the helix is proportional to the wavelength $\lambda_0$ of the selectively reflected light. This relationship can be described by the Bragg diffraction equation, where $n_{mean}$ is the mean refraction index and $\phi$ is the angle of the incident light beam with respect to the normal of the surface:

$$\lambda_0 = L_0 \cdot n_{mean} \cdot \sin \phi$$

If the temperature increases beyond the Blue Start temperature, the molecular structure of the helix disbands and the molecules are uniformly distributed like in an isotropic liquid. In this state, the crystals are optically inactive again. Exceeding the Blue Start temperature may lead to a permanent damage of the TCLCs, depending on time and extent of the overheating.

Figure 8:
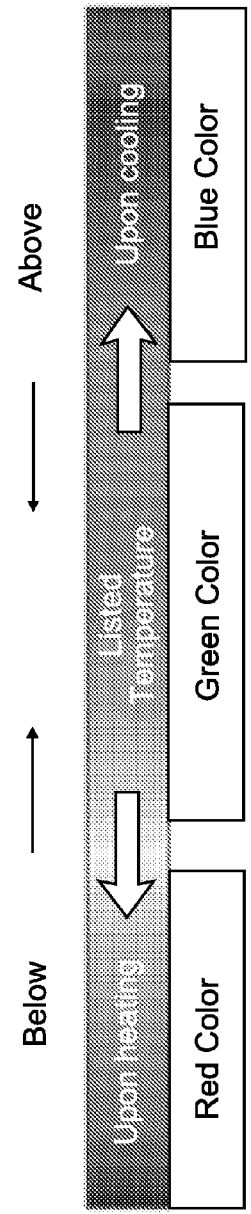
FIG. 8 illustrates the range of the color of the thermochromic liquid crystal depending on temperature.

The bandwidth of the TCLCs is defined as optical active range and is limited downward by a Red-start temperature and upward by a Blue-end temperature. The light passing the liquid crystal undergoes Bragg diffraction on these layers, and the wavelength with the greatest constructive interference is reflected back, which is perceived as a spectral color. As the crystal undergoes changes in temperature, thermal expansion occurs, resulting in change of spacing between the layers, and therefore in the reflected wavelength. The color of the thermochromic liquid crystal can therefore continuously range from black through the spectral colors to black again, depending on the temperature. as shown in FIG. 8.

As the TCLCs only have thermochromic properties when they are in the Cholesteric state, a thermochromic material having a specified temperature range can be engineered by mixing different cholesteric compounds.

To demonstrate the principle of some aspects of employing TCLCs, an experiment was conducted. The first step included preparing some cholesteryl ester liquid crystals using a known method, based on G. H. Brown and J. J. Wolken, Liquid Crystals and Biological Systems, Academic Press, NY, 1979, pp. 165-167 and W. Elser and R. D. Ennulat, Adv. Liq. Cryst. 2, 73 (1976), the contents of which are incorporated herein by reference. The start materials were: (A) Cholesteryl oleyl carbonate, (Aldrich 15,115-7), (B) Cholesteryl pelargonate (Cholesteryl nonanoate) (Aldrich C7,880-1), and (C) Cholesteryl benzoate (Aldrich C7,580-2). Different compositions of the mixture of these three chemicals A, B, and C producing a liquid crystal film change color over different temperature ranges as shown in TABLE 2.

TABLE 2

| A = Cholesteryl oleyl Carbonate, g | B = Cholesteryl pelargonate, g | C = Cholesteryl benzoate, g | Transition range, ° C. |
|---|---|---|---|
| 0.65 | 0.25 | 0.10 | 17-23 |
| 0.70 | 0.10 | 0.20 | 20-25 |
| 0.45 | 0.45 | 0.10 | 26.5-30.5 |
| 0.43 | 0.47 | 0.10 | 29-32 |
| 0.44 | 0.46 | 0.10 | 30-33 |
| 0.42 | 0.48 | 0.10 | 31-34 |
| 0.40 | 0.50 | 0.10 | 32-35 |
| 0.38 | 0.52 | 0.10 | 33-36 |
| 0.36 | 0.54 | 0.10 | 34-37 |
| 0.34 | 0.56 | 0.10 | 35-38 |
| 0.32 | 0.58 | 0.10 | 36-39 |
| 0.30 | 0.60 | 0.10 | 37-40 |

These liquid crystals reversibly change color as the temperature changes. An advantage of liquid crystals is their ability to map out thermal regions of different temperature.

The liquid crystal mixture changes color with temperature. The TCLC film may degrade when exposed to moisture or air, but as long as they are stored in a sealed container the mixture may be prepared months in advance.

The example experimental setup in the demonstration included the TCLC films from Liquid Crystal Resources Inc (Glenview, Ill.), an optical Red-Green-Blue (RGB) sensor and software TCS230EVM from Texas Advanced Optoelectronic Solutions (Plano, Tex.), a programmable heating and cooling plate IC35 from Torrey Pines Scientific, Inc. (San Marcos, Calif.). Several K type thermocouples from Omega Engineering Inc, Stamford Conn. were used to ascertain the temperature on the heating-cooling plate. The TLC film was attached to the heater/cooler plate, and temperature was set at 5-45° C., in 5° C. steps. Three thermocouples were taped to the film and one to the plate. Two different TLC films were used: 5-20° C. and 20-40° C. Both temperature and RGB data were captured at a frequency of 20 Hz using DAQ.

Figure 9:
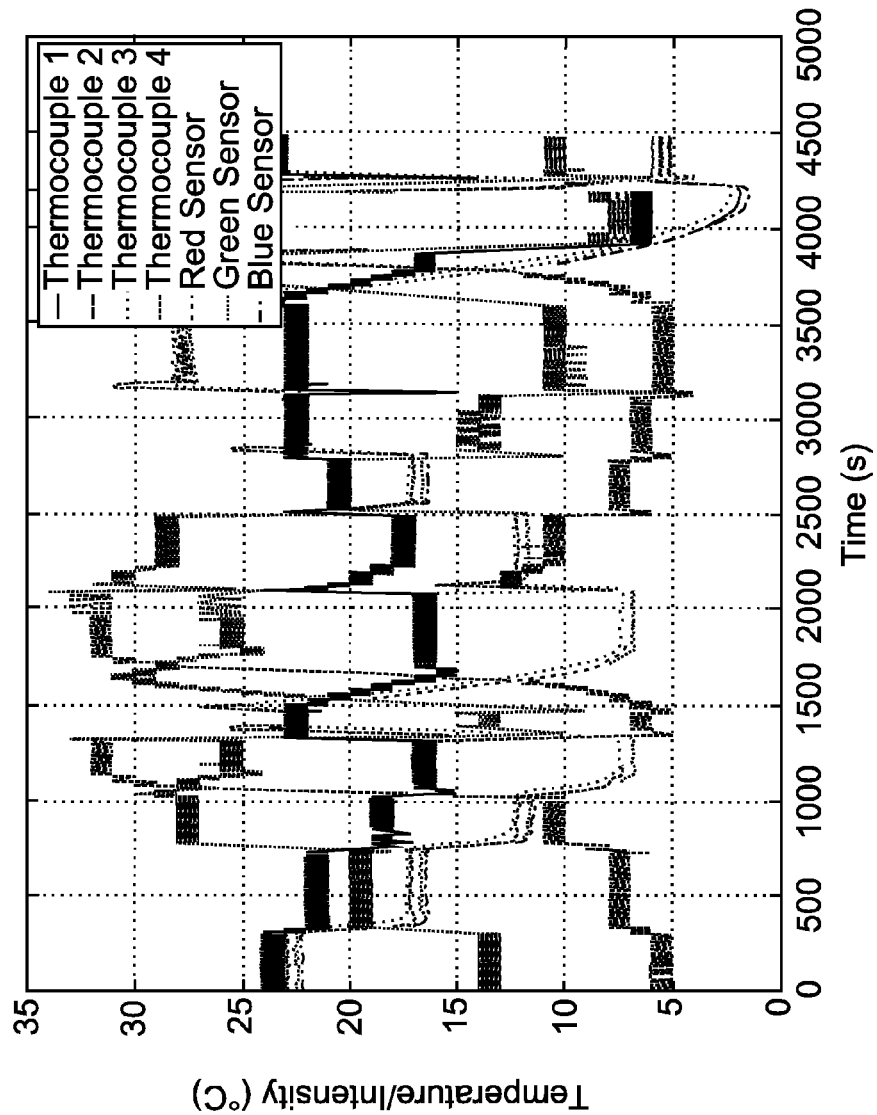
FIG. 9 illustrates a graph of temperature vs. time and optical intensity (RGB) vs. time from an example experimental setup.
Figure 10:
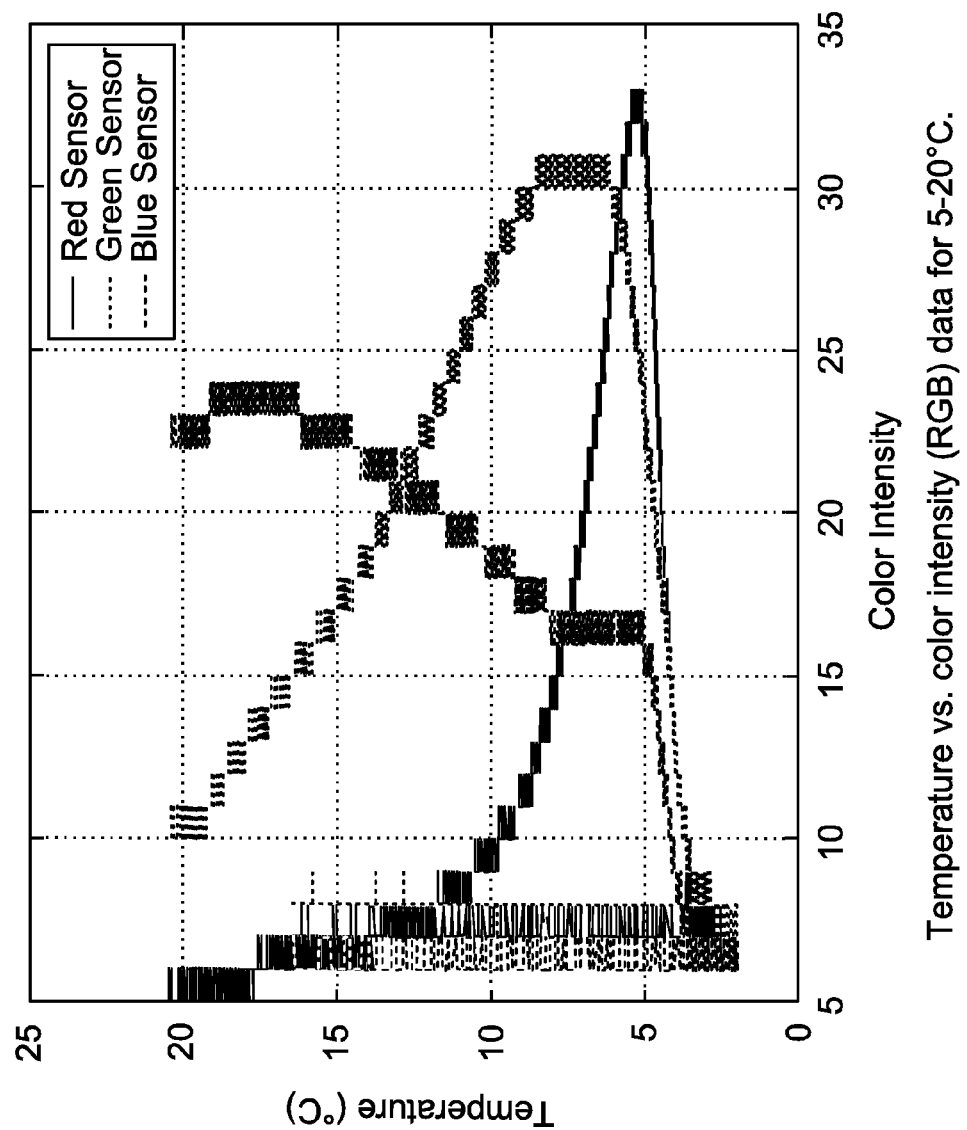
FIG. 10 illustrates a graph of temperature vs. color intensity (RGB) converted from the data of the graph of FIG. 9.

The results of the example experimental setup above are described. The temperature vs. time and optical intensity vs. time data illustrated in FIG. 9 were converted to temperature vs. color intensity data illustrated in FIG. 10.

Figure 11A:
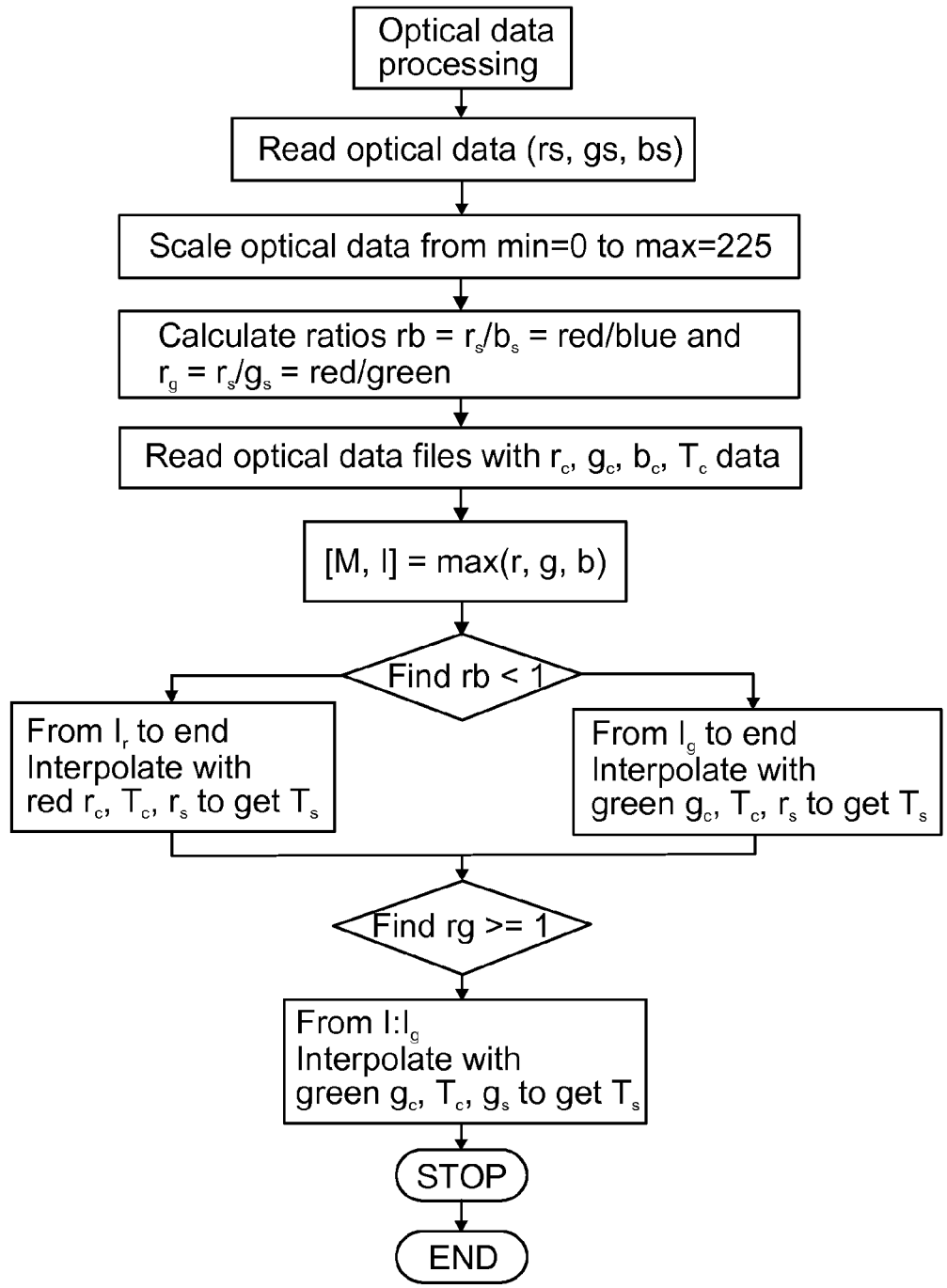
FIG. 11A illustrates a subroutine for optical processing to convert RGB data into temperature data.
Figure 11B:
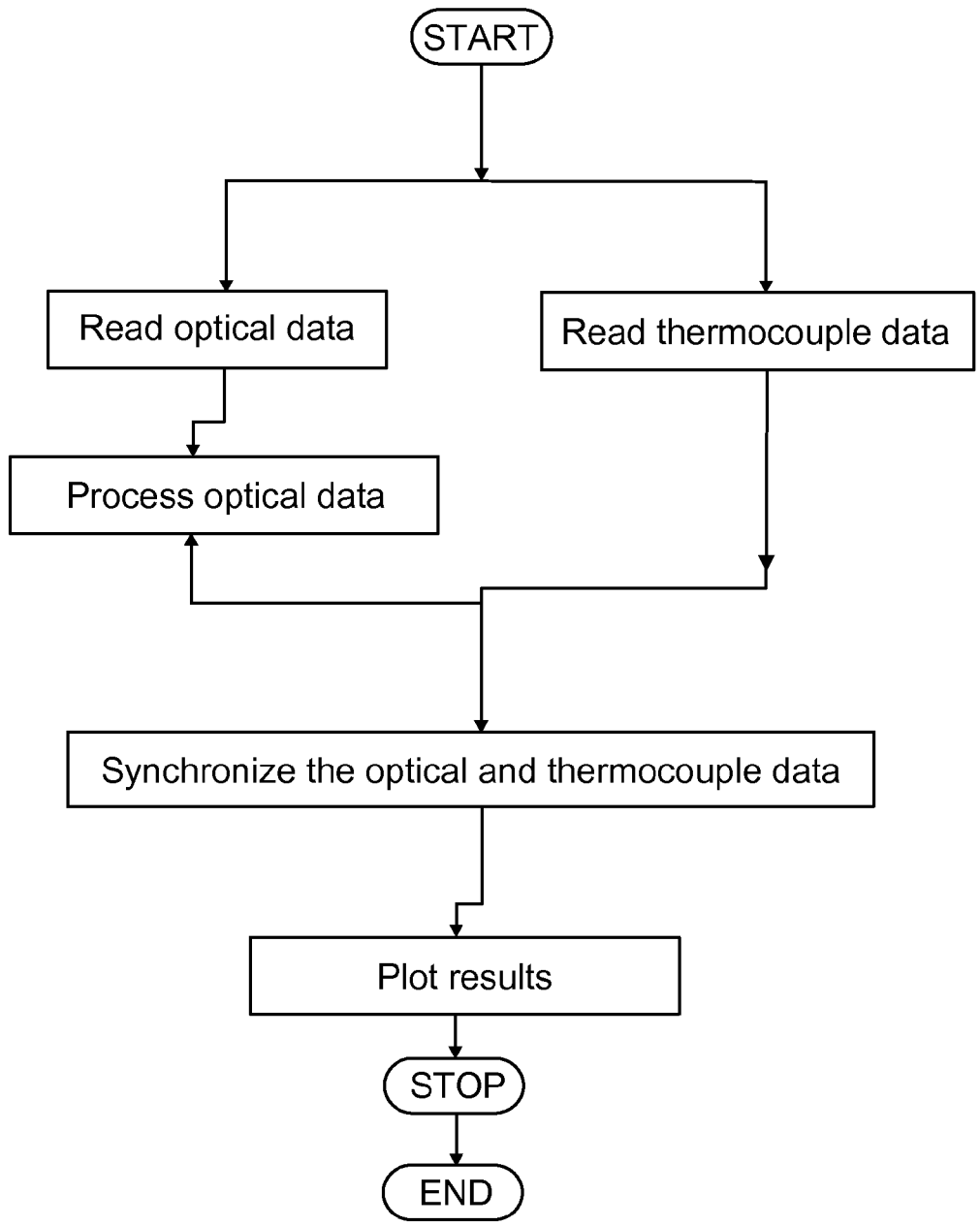
FIG. 11B illustrates a general algorithm to process optical data to convert RGB data into temperature data.

FIG. 11A illustrates a subroutine for optical processing to convert RGB data into temperature data. The optical data acquired is in a three-column format with $r_s$, $g_s$, $b_s$ being the values for red, green and blue sample. The data is used to evaluate the ratios rg and rb. The ratios are then matched to the mapping file which has the calibration data red, green, blue and temperature data $r_c$, $g_c$, $b_c$ and $T_c$. FIG. 11B illustrates a general algorithm to process optical data to convert RGB data into temperature data.

Figure 13:
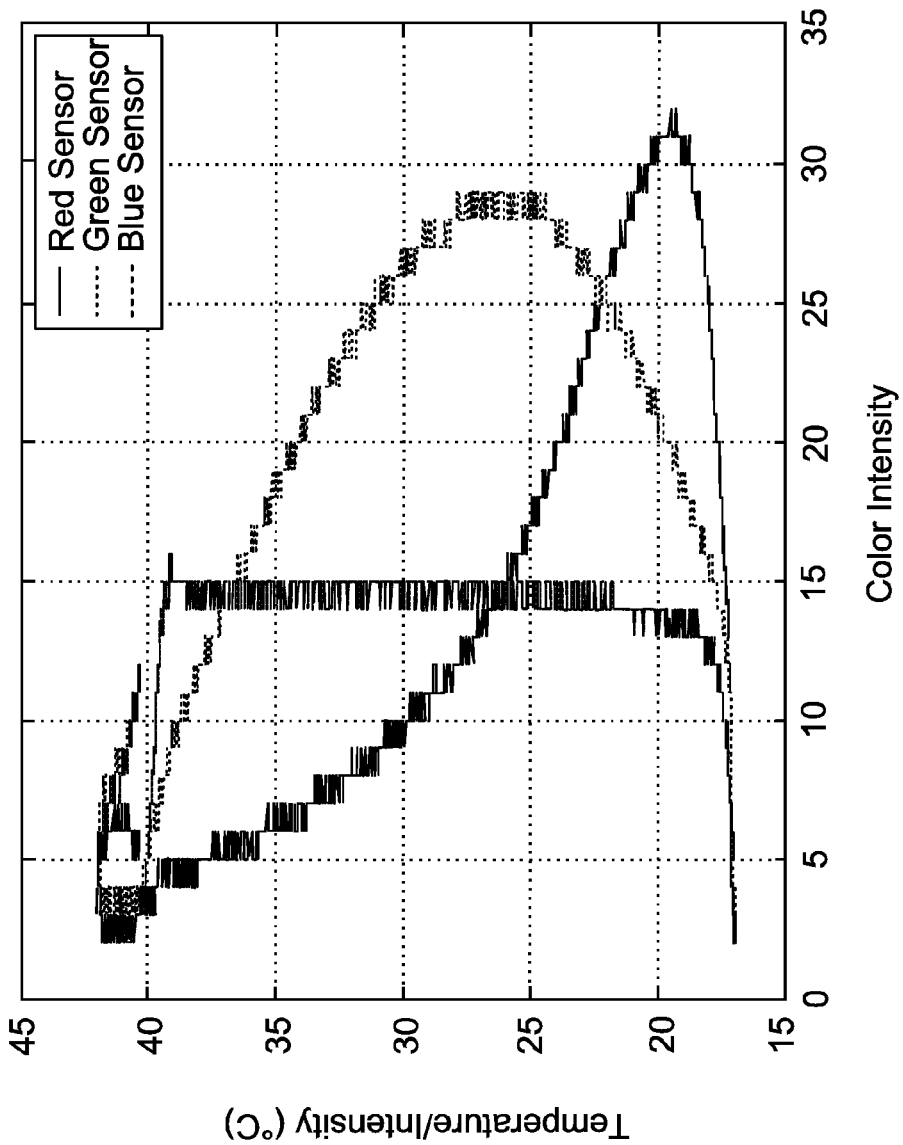
FIG. 13 illustrates a graph of temperature vs. color intensity (RGB) converted from the data of the graph of FIG. 12.
Figure 14:
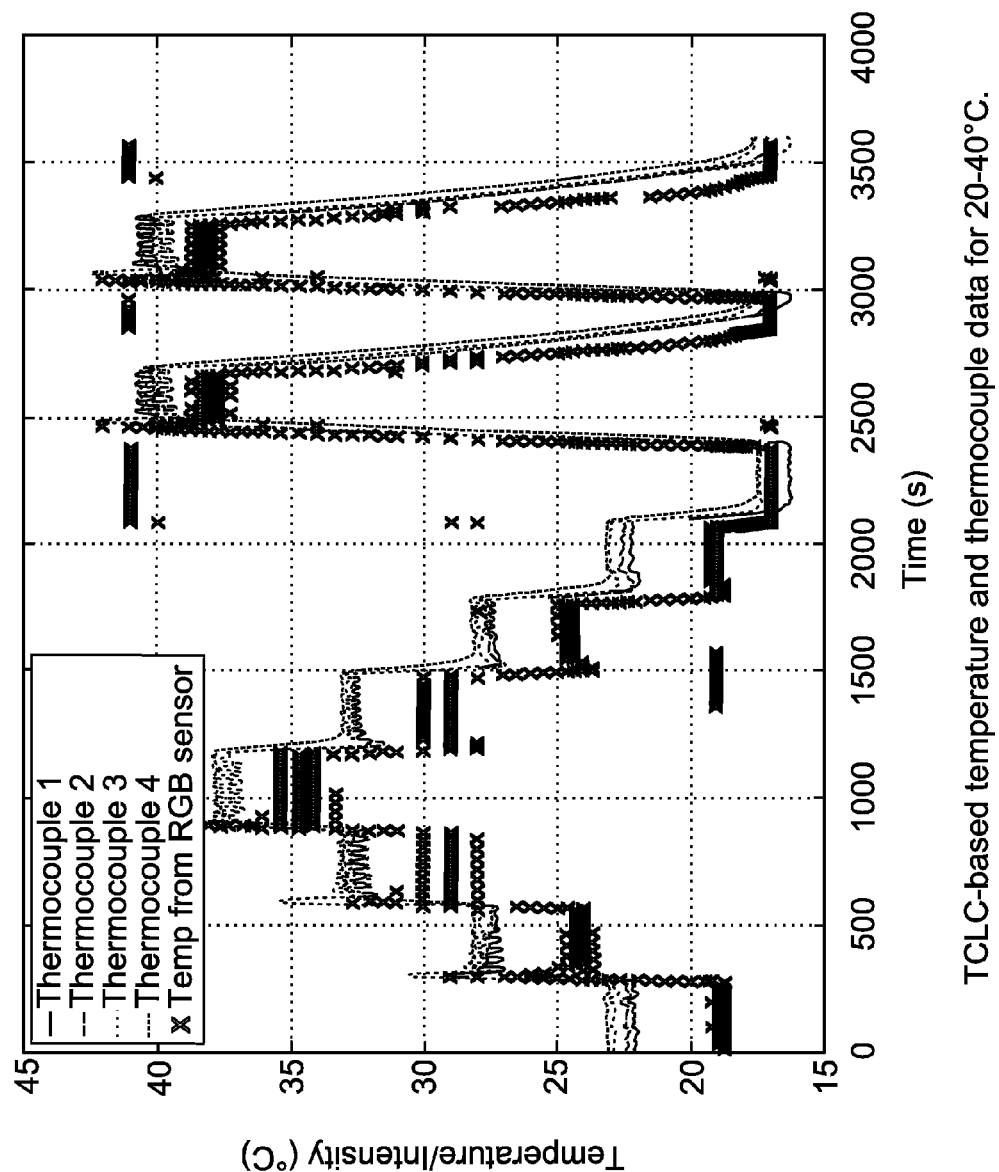
FIG. 14 illustrates TCLC-based temperature and thermocouple data corresponding to the data of FIGS. 12 and 13.
Figure 15:
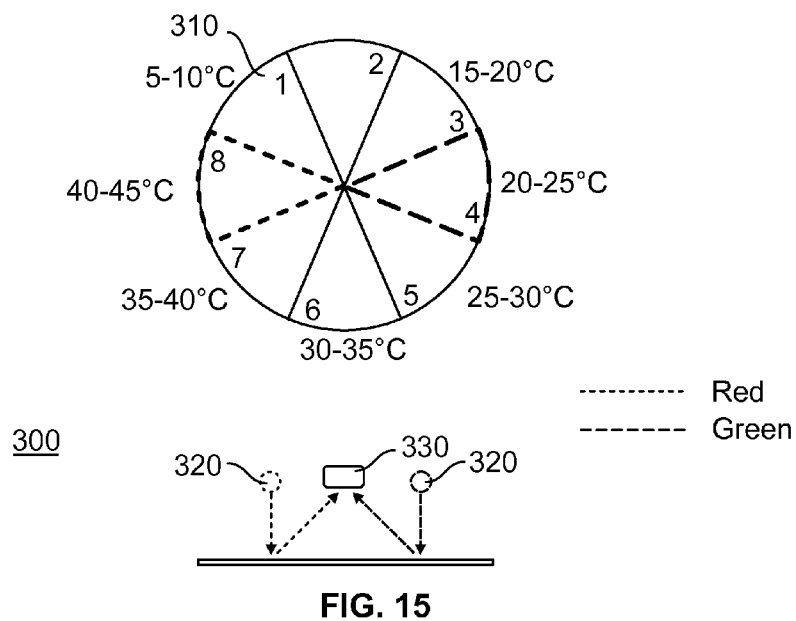
FIG. 15 illustrates a "sliced-pie TCLC configuration" for measuring temperatures with an array of TCLC materials according to aspects of the present invention.

Data for the 20° C. to 40° C. temperature tests are shown in FIG. 12. As shown in FIG. 13, the temperature-time and color intensity-time data are converted to temperature-color intensity data. The TCLC-based temperature are compared with thermocouple data in FIG. 15.

After applying the algorithms of FIGS. 11A and 11B, the temperatures calculated from the RGB sensor follow the thermocouple data closely. Accordingly, the demonstration above shows that optical data can be converted into temperature data and the use of optical data from TCLC film for temperature measurement is feasible. In general, a TCLC film may be used in conjunction with an RGB sensor for measuring the sensor temperature. The change in color of the film may be calibrated to a temperature of the strip. Furthermore, studies have shown that the technique of using a TCLC film works for varying temperature differences between the sensor and the meter. In one aspect, the temperature difference may be approximately 45° C. In another aspect, the temperature difference may be approximately 25° C. In yet another aspect, the temperature difference may be approximately 10° C.

To measure the color of the TCLC, in one embodiment, the optical-sensing system 250B may employ the general configuration shown in FIG. 5. In particular, the light source 252B may be three LEDs corresponding to red, green, and blue wavelengths, or may be a single LED emitting white light. Three separate photodiodes with filters measure the reflection $R_r$, $R_g$, and $R_b$ from the TCLC corresponding to red, green, and blue wavelengths, respectively. The ratio $R_r$:$R_g$:$R_b$ changes according to color change in the TCLC. As the TCLC changes from red to green to blue with increasing temperatures, the ratios $R_r$:$R_b$ and $R_r$:$R_g$ decrease with the increase in temperature. Thus, the temperature of the TCLC may be determined from the ratio $R_r$:$R_g$:$R_b$. Other ratios between $R_r$, $R_g$, and $R_b$ may be employed by other embodiments. In addition, a calibration feature may be required for this embodiment.

In yet another embodiment, the optical-sensing system 250B may also employ the general configuration shown in FIG. 5. However, the light source 252B may be a LED emitting a white light, while the detector 254B may be an integrated red/green/blue (RGB) color sensor detecting the level of red, green, and blue light reflecting from the TCLC. The amounts of red, green, and blue light indicate the color and thus the temperature of the TCLC.

In a further embodiment, the optical-sensing system 250B also employs the general configuration shown in FIG. 5. In this embodiment, the light source 252B may be a LED emitting photons of a certain wavelength, while the detector 254B may be a photodiode measuring the reflection of photons of the certain wavelength. The amount of reflection changes as the color of the TCLC changes. Thus, the measured reflection indicates the temperature of the TCLC.

Rather than using the general configuration of FIG. 5, the optical-sensing system 250B in an alternative embodiment may employ an assembly that integrates illumination optics and receiver circuitry, including a red/green/blue (RGB) color sensor. This "hybrid" assembly, or combined structure, employs separate LED light sources to transmit red, green, and blue light to the TCLC. The reflected signal for each color may then be measured and converted into 16-bit data, for example, to enable color recognition, and thus a temperature reading, by the processing system 230.

Although the embodiments described herein provide more accurate temperature readings than conventional systems, it has been discovered that further accuracy may be achieved by optimal positioning of the sensor of the temperature-measuring system 250 within the test-sensor opening 210. For example, as shown in FIG. 3E, the thermopile sensor 250A occupies a position 251 within the test-sensor opening 210. In some embodiments, this may mean that the sensor 250A is positioned near the electrical contacts that receive the test sensor electrodes. When the thermopile sensor 250A is positioned more deeply within the interior of the meter 210 in the direction X shown FIG. 3E, the thermopile sensor 250A measures the temperature at a region 113 of the meter-contact area 112 where heat transfer from the meter 200 is minimized. In one aspect, convective heat transfer is reduced at positions deeper within the test-sensor opening 210. Thus, the temperature at a region deeper within the test-sensor opening 210 changes more slowly, so that there is a greater chance of obtaining an accurate measurement of the temperature of the test sensor 100 without the effects of heat transfer from the meter 200.

In the embodiments described herein, heat transfer to the measured region 113 on the test sensor 100 may also be minimized by providing a space between the region 113 and the thermopile sensor 250A to create an insulating air pocket around the region 113. In addition, conductive heat transfer to the test sensor 100 may be reduced by employing point contacts, rather than surface contacts, where any contact between the meter 200 and the test sensor 100 is necessary.

In general, the meter 200 employs an architecture that combines an analog front end with a digital engine. Typically, the analog front end relates to components such as the measurement system 220. Meanwhile, the digital engine executes data processing functions and controls electronic components such as the user interface 240. It is contemplated that the architecture in the embodiments described herein can be configured so that the temperature-measuring system 250 may be integrated with the analog front end or the digital engine. Advantageously, when the temperature-measuring system 250 is integrated with the analog front end, fewer electronic components are required for designing and implementing the temperature-measuring system 250. On the other hand, when temperature-measuring system 250 is integrated with the digital engine, the architecture enables different configurations for an analog front end to be designed and implemented with the digital engine without having to design each front end configuration to handle temperature measurement functions.

Although the embodiments described herein may measure the temperature of one or more areas of a test sensor to determine the temperature of a reagent disposed on the test sensor, it is contemplated that the temperature of the reagent may be measured directly according to the techniques described. For example, a thermochromic material may be applied at or near the reagent to measure the temperature of the reagent.

Figure 17:
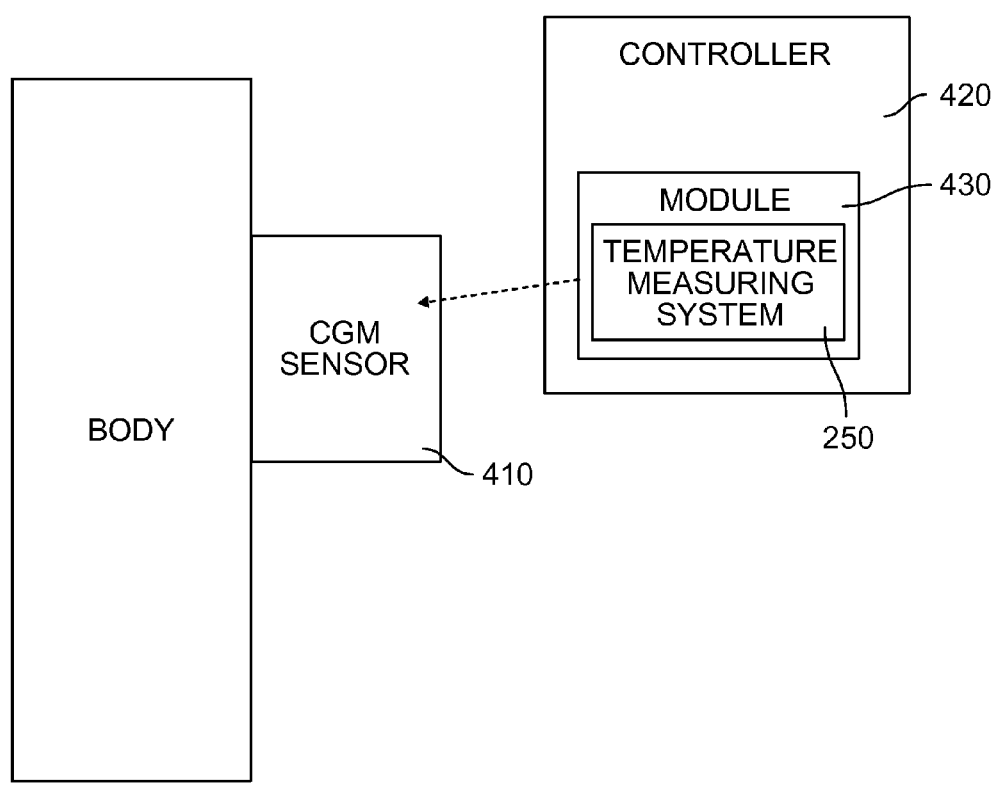
FIG. 17 illustrates a system for calibrating a device, such as a CGM sensor, with a controller having a temperature-measuring system according to aspects of the present invention.

The temperature measurement techniques described herein may also be used in a controller employed in combination with a continuous glucose monitoring (CGM) system 400 as shown in FIG. 17. Typically in the CGM system 400, a CGM sensor 410 is attached to a user. The CGM sensor 410 may be placed in contact or optical communication with the user's blood or interstitial fluid to measure a desired analyte concentration in the sample. The CGM sensor 410 may measure a desired analyte concentration of the user through the skin. Once the CGM sensor 410 has measured a analyte concentration, i.e., glucose, as known to those in the art, a signal is sent to a controller 420 or similar device. The CGM system 400 may take measurements at different time intervals. As illustrated, the controller 420 is remote from the CGM sensor 410 in FIG. 17, but in other embodiments, the controller 420 may be attached to the CGM sensor 410. However, most CGM systems must be calibrated at different time intervals such that the CGM system produces a more accurate value. To calibrate the CGM system 400, a discrete blood glucose meter, such as the embodiments described above, may be used to provide an accurate reading at a given time frame. The reading can then be used to calibrate CGM system 400. The meter used for such a task may be a meter 200 or other meters described previously herein or the meter may simply be a module 430 that is contained within controller 420. The controller 420 provides similar functions as meter 200 and has like components as previous embodiments discussed herein. The module 430 may be integral with controller 420 or simply be a component part that is added into the controller. The module 430 has an opening 432 to receive a test sensor strip, which may be similar to sensor 100 or other embodiments as previously described herein and can calculate the concentration of glucose in a sample as earlier described with reference to previous embodiments. In an alternate embodiment, some of the software or other electrical components required to calculate the concentration of glucose in the sample may be contained on the controller 420 apart from the module 430. In either case the module 430 may have a connector 434 that electrically or optically connects the module 430 to the controller 420. The controller may also have a display 440 so as to display the measured glucose reading.

Figure 16:
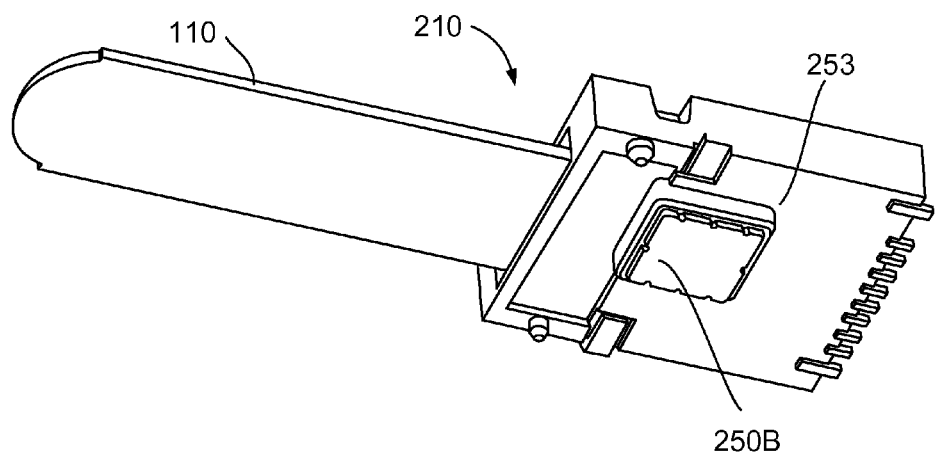
FIG. 16 illustrates an integrated connector and IR sensor according to aspects of the present invention.

The module 430, similar to previous embodiments may include one or more temperature measuring systems 250. The temperature measuring system 250 may employ the measurement techniques described herein or may include aspects of the temperature measuring systems described herein. For example, the temperature measuring system 250 may include a thermopile sensor or employ a TCLC measurement system to provide more accurate measurements that account for temperature effects. The components may be positioned or configured similarly as previously discussed. In another embodiment, however, FIG. 16 illustrates a configuration that integrates or embeds an optical-sensing system 250B, such as an infrared (IR) sensor, with a connector 253 that can be coupled to the module 430, where the optical-sensing system 250B is positioned to measure a temperature of the test sensor 110 in a test-sensor opening 210 as described previously, for example.

Alternative Embodiment A

An assembly for determining an analyte concentration in a fluid sample, comprising:
a test sensor comprising a fluid-receiving area for receiving a fluid sample, the fluid-receiving area containing a reagent that produces a measurable reaction with an analyte in the sample, the test sensor having a test-sensor temperature and the reagent having a reagent temperature;
a meter comprising:
an opening configured to receive the test sensor;
a measurement system configured to determine a measurement of the reaction between the reagent and the analyte; and
a temperature-measuring system configured to determine a measurement of the test-sensor temperature when the test sensor is received into the opening,
wherein the meter determines a concentration of the analyte in the sample using the measurement of the reaction and the measurement of the test-sensor temperature.

Alternative Embodiment B

The assembly of embodiment A, wherein the temperature-measuring system comprises a thermopile sensor configured to determine a measurement of the test-sensor temperature by measuring infrared radiation from the test sensor.

Alternative Embodiment C

The assembly of embodiment B, wherein the temperature-measuring system further comprises at least one of a thermistor, thermocouple, and a semiconductor temperature sensor configured to determine a measurement of a reference temperature corresponding to a body of the meter.

Alternative Embodiment D

The assembly of embodiment A, wherein the test sensor includes a thermochromic material applied thereto.

Alternative Embodiment E

The assembly of embodiment D, wherein the temperature-measuring assembly comprises an optical-sensing system configured to detect a temperature dependent color of the thermochromic material.

Alternative Embodiment F

The system of embodiment A, wherein the test-sensor temperature and the reagent temperature are at about ambient temperature.

Alternative Embodiment G

The system of embodiment A, wherein the opening extends from a first end proximate to an exterior surface of the meter to a second end in an interior of the meter, and the temperature-measuring assembly includes a temperature sensor that is positioned near the second end to minimize heat transfer to a region of the test sensor being measured by the temperature sensor.

Alternative Embodiment H

The system of embodiment A, wherein the temperature-measuring assembly includes a temperature sensor that receives a temperature-related signal from a region of the test sensor, and the temperature sensor and the region of the test sensor are separated by a space, the space forming an insulating air pocket around the region to minimize heat transfer to the region.

Alternative Embodiment I

The system of embodiment A, wherein any contact between the meter and the test sensor is a point contact to minimize heat transfer from the meter to the test sensor.

Alternative Embodiment J

A method for determining an analyte concentration in a sample of body fluid, comprising the steps of:

placing a test sensor into an opening, the test sensor comprising a fluid-receiving area for receiving a sample of body fluid, the fluid-receiving area containing a reagent that produces a measurable reaction with an analyte in the sample, the test sensor having a test-sensor temperature and the reagent having a reagent temperature;

determining a measurement of the test-sensor temperature when the test sensor is received into the opening; and determining a concentration of the analyte in the sample according to the measurement of the reaction and the measurement of the test-sensor temperature.

Alternative Embodiment K

The method of embodiment J, wherein the step of determining a measurement of the test-sensor temperature comprises measuring the test-sensor temperature with a thermopile sensor, the thermopile sensor measuring infrared radiation from the test sensor.

Alternative Embodiment L

The method of embodiment K, further comprising the step of determining a measurement of a reference temperature using a thermistor.

Alternative Embodiment M

The method of embodiment J, wherein the test sensor includes a thermochromic material applied thereto.

Alternative Embodiment N

The method of embodiment M, wherein the step of determining a measurement of the test-sensor temperature comprises measuring the test-sensor temperature with an optical-sensing system, the optical-sensing system configured to detect a temperature dependent color of the thermochromic material.

Alternative Embodiment O

The method of embodiment J, wherein the test-sensor temperature and the reagent temperature are at about an ambient temperature.

Alternative Embodiment P

The method of embodiment J wherein the opening extends from a first end proximate to an exterior surface of the meter to a second end in an interior of the meter, and the act of placing a test sensor into an opening comprises positioning a temperature sensor near the second end to minimize heat transfer to a region of the test sensor being measured by the temperature sensor.

Alternative Embodiment Q

The method of embodiment J wherein the act of determining a measurement of the test-sensor temperature comprises receiving, via a temperature sensor, a temperature-related signal from a region of the test sensor, and the act of placing a test sensor into an opening comprises providing a space between the temperature sensor and the region of the test sensor, the space forming an insulating air pocket around the region to minimize heat transfer to the region.

Alternative Embodiment R

The method of embodiment J, wherein any contact between the meter and the test sensor is a point contact to minimize heat transfer from the meter to the test sensor.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

What is claimed is:

1. A meter for determining an analyte concentration in a fluid sample received on a test sensor, the test sensor comprising a fluid-receiving area for receiving the fluid sample, the fluid-receiving area containing a reagent that produces a measurable reaction with an analyte in the sample, the test sensor having a test-sensor temperature and the reagent having a reagent temperature, the meter comprising:

an opening configured to receive the test sensor such that a region of the test sensor is disposed inside the meter and the fluid-receiving area of the test sensor is disposed outside the meter;

a measurement system configured to determine a measurement of the reaction between the reagent and the analyte; and a temperature-measuring system including a temperature sensor configured to determine a measurement of the test-sensor temperature when the test sensor is received into the opening, the temperature sensor measuring the region of the test sensor disposed inside the meter while the fluid-receiving area is disposed outside the meter, wherein the meter determines a concentration of the analyte in the sample using the measurement of the reaction and the measurement of the test-sensor temperature.

2. The meter of claim 1, wherein the opening extends from a first end proximate to an exterior surface of the meter to a second end in an interior of the meter, and the temperature sensor is positioned near the second end to minimize heat transfer to the region of the test sensor being measured by the temperature sensor.

3. The meter of claim 1, wherein the temperature sensor receives a temperature-related signal from the region of the test sensor being measured, and the temperature sensor and the region of the test sensor are separated by a space, the space forming an insulating air pocket around the region to minimize heat transfer to the region.

4. The meter of claim 1, further comprising at least one point contact to contact the test sensor while minimizing heat transfer from the meter to the test sensor.

5. The meter of claim 1, wherein the temperature sensor is disposed inside the meter and configured to measure the region of the test sensor disposed inside the meter.

6. A method for determining an analyte concentration in a sample of body fluid, comprising the steps of:

placing a test sensor into an opening of a meter, the opening being configured to receive the test sensor, the test sensor comprising a fluid-receiving area for receiving a sample of body fluid, the fluid-receiving area containing a reagent that produces a measurable reaction with an analyte in the sample, the test sensor having a test-sensor temperature and the reagent having a reagent temperature;

estimating a measurement of the test-sensor temperature when the test sensor is received into the opening by measuring, with a temperature sensor, a region of the test-sensor when the region is disposed inside the meter and the fluid-receiving area of the test sensor is disposed outside the meter;

measuring the reaction between the reagent and the analyte in the sample; and determining a concentration of the analyte in the sample according to the measurement of the reaction and the measurement of the test-sensor temperature.

7. The method of claim 6, wherein the opening extends from a first end proximate to an exterior surface of the meter to a second end in an interior of the meter, and the act of placing a test sensor into an opening comprises positioning the temperature sensor near the second end to minimize heat transfer to the region of the test sensor being measured by the temperature sensor.

8. The method of claim 6, wherein the act of determining a measurement of the test-sensor temperature comprises receiving, via the temperature sensor, a temperature-related signal from the region of the test sensor being measured, and the act of placing a test sensor into an opening comprises providing a space between the temperature sensor and the region of the test sensor, the space forming an insulating air pocket around the region to minimize heat transfer to the region.

9. The method of claim 6, wherein any contact between the meter and the test sensor is a point contact to minimize heat transfer from the meter to the test sensor.

10. The method of claim 6, wherein the temperature sensor is disposed inside the meter and configured to measure the region of the test sensor disposed inside the meter.

11. The method of claim 6, wherein the test-sensor temperature and the reagent temperature are at about an ambient temperature.

* * * * *